(12) United States Patent
Dacosta et al.

(10) Patent No.: US 12,178,454 B2
(45) Date of Patent: *Dec. 31, 2024

(54) TARGETING INSTRUMENTS, SYSTEMS AND METHODS OF USE

(71) Applicant: Paragon 28, Inc., Englewood, CO (US)

(72) Inventors: Albert Dacosta, Lone Tree, CO (US); Eric Lintula, Parker, CO (US); Frank S. Bono, Castle Rock, CO (US); Frank Barmes, Parker, CO (US); Joseph Dogué, Aurora, CO (US); Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/483,771

(22) Filed: Oct. 10, 2023

(65) Prior Publication Data

US 2024/0032948 A1 Feb. 1, 2024

Related U.S. Application Data

(63) Continuation of application No. 17/456,276, filed on Nov. 23, 2021, now Pat. No. 11,779,358, which is a continuation of application No. 15/908,048, filed on Feb. 28, 2018, now Pat. No. 11,179,168, which is a continuation of application No. PCT/US2018/020053, filed on Feb. 27, 2018.

(60) Provisional application No. 62/464,051, filed on Feb. 27, 2017.

(51) Int. Cl.
*A61B 17/17* (2006.01)
*A61B 17/72* (2006.01)

(52) U.S. Cl.
CPC ...... *A61B 17/1775* (2016.11); *A61B 17/1717* (2013.01); *A61B 17/1728* (2013.01); *A61B 17/7291* (2013.01)

(58) Field of Classification Search
CPC . A61B 17/17; A61B 17/1717; A61B 17/1728; A61B 17/1775
See application file for complete search history.

(56) References Cited

U.S. PATENT DOCUMENTS

| 2,526,959 A | 10/1950 | Lorenzo |
| 4,341,206 A | 7/1982 | Perrett |
| 5,350,380 A | 9/1994 | Goble |

(Continued)

FOREIGN PATENT DOCUMENTS

| EP | 0468192 | 1/1992 |
| EP | 0617927 | 10/1994 |

(Continued)

OTHER PUBLICATIONS

Budny et al. "Naviculocuneiform Arthrodesis," Clinics in Podiatric Medicine and Surgery, vol. 24, pp. 753-763, Oct. 2007.

(Continued)

*Primary Examiner* — Si Ming Ku
(74) *Attorney, Agent, or Firm* — Heslin Rothenberg Farley & Mesiti P.C.; Jacquelyn A. Graff, Esq.

(57) ABSTRACT

Instruments, implants, bone plates, systems and methods for correcting bone deformities and fractures in the lower extremity are disclosed. Specifically, targeting instruments, implants, bone plates, systems and methods used for correcting bone deformities and/or fractures in the foot are disclosed.

16 Claims, 31 Drawing Sheets

(56) References Cited

U.S. PATENT DOCUMENTS

| | | | |
|---|---|---|---|
| 5,352,228 A | 10/1994 | Kummer | |
| 5,429,641 A | 7/1995 | Gotfried | |
| 5,458,602 A | 10/1995 | Goble | |
| 5,688,284 A | 11/1997 | Chervitz | |
| 6,342,057 B1 | 1/2002 | Brace | |
| 6,692,496 B1 | 2/2004 | Wardlaw | |
| 7,011,665 B2 | 3/2006 | Null | |
| 7,785,326 B2 | 8/2010 | Green | |
| 7,819,877 B2 | 10/2010 | Guzman | |
| 8,206,389 B2 | 6/2012 | Huebner | |
| 8,231,627 B2 | 7/2012 | Huebner | |
| 9,161,796 B2 | 10/2015 | Chiodo | |
| 9,241,744 B2 | 1/2016 | Blake | |
| 9,421,103 B2 | 8/2016 | Jeng | |
| 2003/0009217 A1 | 1/2003 | McKernan | |
| 2004/0102776 A1 | 5/2004 | Huebner | |
| 2004/0102777 A1 | 5/2004 | Huebner | |
| 2005/0027296 A1 | 2/2005 | Thramann | |
| 2005/0033301 A1 | 2/2005 | Lombardo | |
| 2005/0216008 A1 | 9/2005 | Zwirnmann | |
| 2006/0069394 A1 | 3/2006 | Weiler | |
| 2006/0189996 A1 | 8/2006 | Orbay | |
| 2007/0173843 A1 | 7/2007 | Matityahu | |
| 2007/0225714 A1 | 9/2007 | Gradl | |
| 2007/0239168 A1 | 10/2007 | Kuenzi | |
| 2007/0270850 A1 | 11/2007 | Geissler | |
| 2008/0015590 A1 | 1/2008 | Sanders | |
| 2008/0188852 A1 | 8/2008 | Matityahu | |
| 2009/0088767 A1 | 4/2009 | Leyden | |
| 2009/0093849 A1 | 4/2009 | Grabowski | |
| 2009/0171398 A1 | 7/2009 | Phillips | |
| 2010/0087824 A1 | 4/2010 | Collazo | |
| 2010/0121324 A1 | 5/2010 | Tyber | |
| 2011/0144647 A1 | 6/2011 | Appenzeller | |
| 2011/0218576 A1 | 9/2011 | Galm | |
| 2011/0224734 A1 | 9/2011 | Schelling | |
| 2011/0264149 A1 | 10/2011 | Pappalardo | |
| 2011/0270319 A1 | 11/2011 | Sheffer | |
| 2011/0282397 A1 | 11/2011 | Richter | |
| 2012/0078252 A1 | 3/2012 | Huebner | |
| 2012/0109217 A1 | 5/2012 | Perineau | |
| 2012/0209268 A1 | 8/2012 | Overes | |
| 2012/0303038 A1 | 11/2012 | Durante | |
| 2012/0316562 A1 | 12/2012 | Costa | |
| 2013/0018424 A1 | 1/2013 | Subik | |
| 2013/0150903 A1 | 6/2013 | Vincent | |
| 2013/0172942 A1 | 7/2013 | Lewis | |
| 2014/0066996 A1 | 3/2014 | Price | |
| 2014/0107798 A1 | 4/2014 | Jeng | |
| 2014/0114322 A1 | 4/2014 | Perez, III | |
| 2014/0180348 A1 | 6/2014 | Thoren | |
| 2015/0025573 A1 | 1/2015 | Abitbol | |
| 2015/0032168 A1* | 1/2015 | Orsak | A61B 17/68 606/304 |
| 2015/0150683 A1 | 6/2015 | Donner | |
| 2015/0182267 A1 | 7/2015 | Wolf | |
| 2015/0245923 A1 | 9/2015 | Abdou | |
| 2015/0359580 A1 | 12/2015 | Dacosta | |
| 2016/0030064 A1 | 2/2016 | Dacosta | |
| 2016/0135858 A1 | 5/2016 | Dacosta | |
| 2016/0235414 A1 | 8/2016 | Hatch | |
| 2016/0310191 A1 | 10/2016 | Seykora | |
| 2016/0324552 A1 | 11/2016 | Baker | |
| 2016/0354128 A1 | 12/2016 | Jeng | |
| 2017/0216043 A1 | 8/2017 | Surma | |
| 2018/0110530 A1 | 4/2018 | Wagner | |
| 2019/0015140 A1 | 1/2019 | DaCosta | |
| 2019/0038326 A1 | 2/2019 | Hedgeland | |

FOREIGN PATENT DOCUMENTS

| | | |
|---|---|---|
| EP | 1273271 | 8/2007 |
| EP | 3023068 | 5/2016 |
| FR | 3030221 | 6/2016 |
| JP | 04250156 | 9/1992 |
| JP | 2009112594 | 5/2009 |
| WO | 1994015556 | 7/1994 |
| WO | 2009052294 | 4/2009 |
| WO | 2012103335 | 8/2012 |
| WO | 2013009574 | 1/2013 |
| WO | 2015138542 | 9/2015 |
| WO | 2017004221 | 1/2017 |

OTHER PUBLICATIONS

Kamat et al. "Laparoscopic extraction of fractured Kirschner wire from the pelvis," Journal of Minimal Access Surgery, vol. 10, No. 2, pp. 97-98, Jun. 2014.

* cited by examiner

TARGETING INSTRUMENTS, SYSTEMS AND METHODS OF USE

CROSS-REFERENCE TO RELATED APPLICATION

This application is a continuation of U.S. application Ser. No. 17/456,276 filed Nov. 23, 2021 and entitled Targeting Instruments, Systems and Methods of Use, which issues as U.S. Pat. No. 11,779,358 on Oct. 10, 2023, which is a continuation of U.S. application Ser. No. 15/908,048 filed Feb. 28, 2018 and entitled Targeting Instruments, Systems and Methods of Use, which issued as U.S. Pat. No. 11,179,168 on Nov. 23, 2021, which is a continuation of International Application No. PCT/US2018/020053 filed on Feb. 27, 2018 and entitled Targeting Instruments, Systems and Methods of Use, which claims priority benefit under 35 U.S.C. § 119(e) of U.S. Provisional Application No. 62/464,051 filed Feb. 27, 2017 and entitled Targeting Instruments, Systems and Methods of Use, which are incorporated herein by reference in their entireties.

FIELD OF THE INVENTION

The present invention relates generally to general surgery, podiatric, and orthopaedic instruments used for correcting bone deformities. More specifically, but not exclusively, the present invention relates to instruments, implants, plates, systems and methods for correcting bone deformities.

BACKGROUND OF THE INVENTION

Many currently available instruments used in conjunction with implants for correcting bone deformities and fractures use various alignment mechanisms. The currently available instruments may experience problems with adequate surgical exposure, alignment variability, inaccurate targeting and instability. Thus, new instruments and methods of use are needed to ensure proper and reproducible orientation of corrective or stabilization devices to be implanted into the foot and ankle.

SUMMARY OF THE INVENTION

Aspects of the present invention provide instruments, implants, plates, systems and methods for correcting bone deformities in the foot.

In one aspect, provided herein is a targeting guide. The targeting guide includes a guide arm, at least one target member, at least one implant holder and a guide pin.

In another aspect, provided herein is a method of using the targeting guide to secure two bones together. The method includes, inserting the guide pin in a bone. The method also includes securing the guide arm to the guide pin at the second end. In addition, the method includes inserting the protector member into the first end of the guide arm and then inserting the target pin through the at least two bones that the user wants to secure. Next, the method may including drilling a hole over the target pin and threading the target member into the drill hole to secure the two bones. The method may also include removing the guide pin, the target pin and the guide arm. Alternatively, the method may further include attaching an implant holder to the guide arm, securing the implant to the implant holder and positioning the implant over a target location that may be the two bones to be secured.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
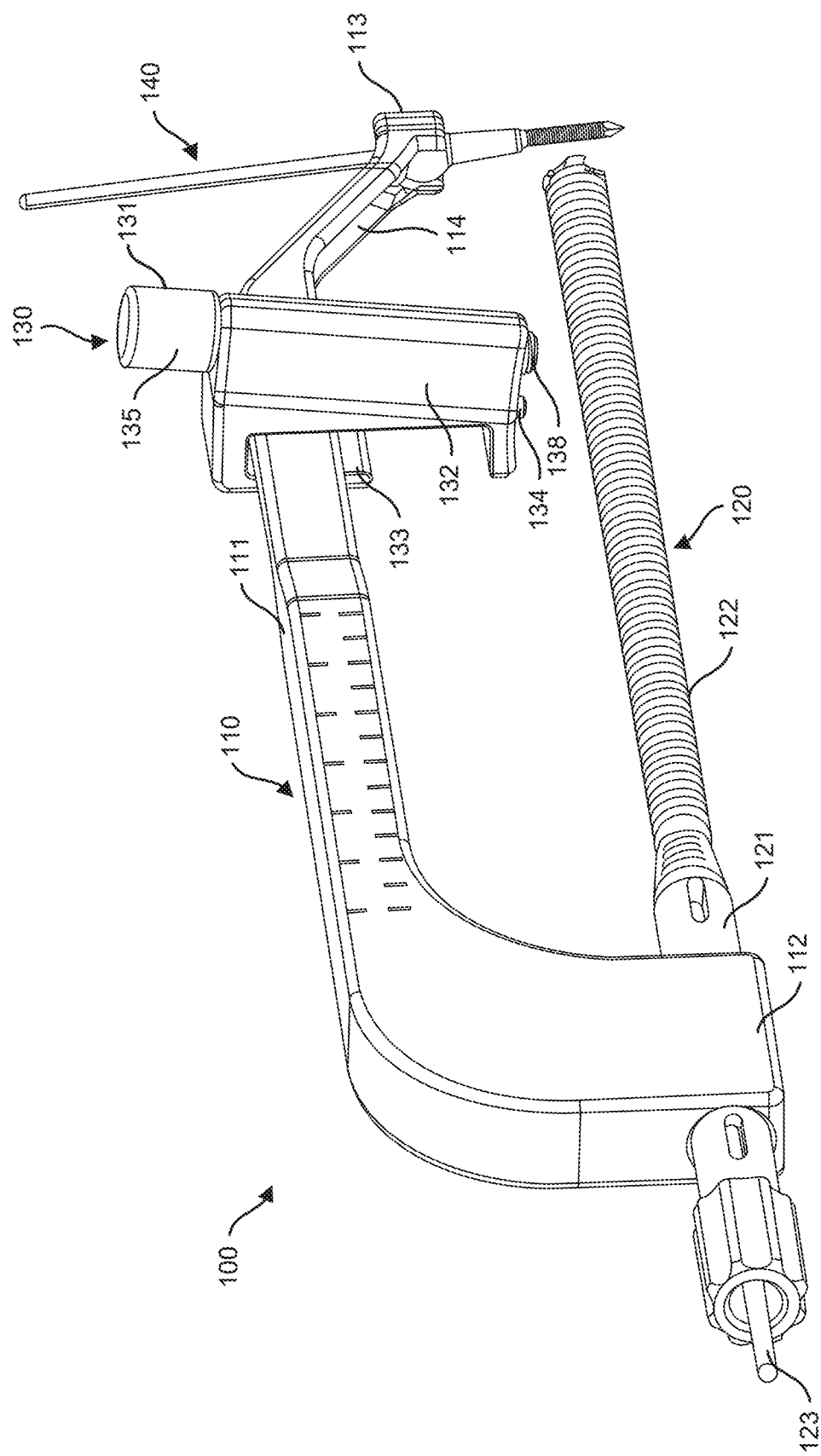
FIG. 1 is a side perspective view of one embodiment of a targeting guide, in accordance with an aspect of the present invention.

Generally stated, disclosed herein are instruments, implants, plates, and systems for correcting bone deformities. Further, methods for correcting bone deformities using instruments, implants, plates, and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current instrumentation and methods are described herein with reference to use with the bones of the foot, the bones of the foot, ankle and lower leg may be used to describe the surfaces, positions, directions or orientations of the instrumentation and methods. Further, the instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the instrumentation and methods, and the aspects, components, features and the like thereof, described herein with respect to the right foot may be mirrored so that they likewise function with the left foot. Further, the instrumentation and methods, and the aspects, components, features and the like thereof, disclosed herein are described with respect to the foot for brevity purposes, but it should be understood that the instrumentation and methods may be used with other bones of the body having similar structures.

As shown in FIGS. 1-5, the targeting guide assembly may include a guide arm 110, a target member 120, an implant holder 130 and a guide pin 140. As seen FIGS. 1-2, the target member 120 extends through a through hole 116 positioned at a first end 112 of the guide arm 110 and runs generally parallel to an elongate body or body 111 of the guide arm 110. The first end 112 of the guide arm 110 with the through hole 116 allows for ease of insertion and removal of the target member 120 to accommodate various clinical circumstances and/or anatomic positions within the foot.

Figure 2:
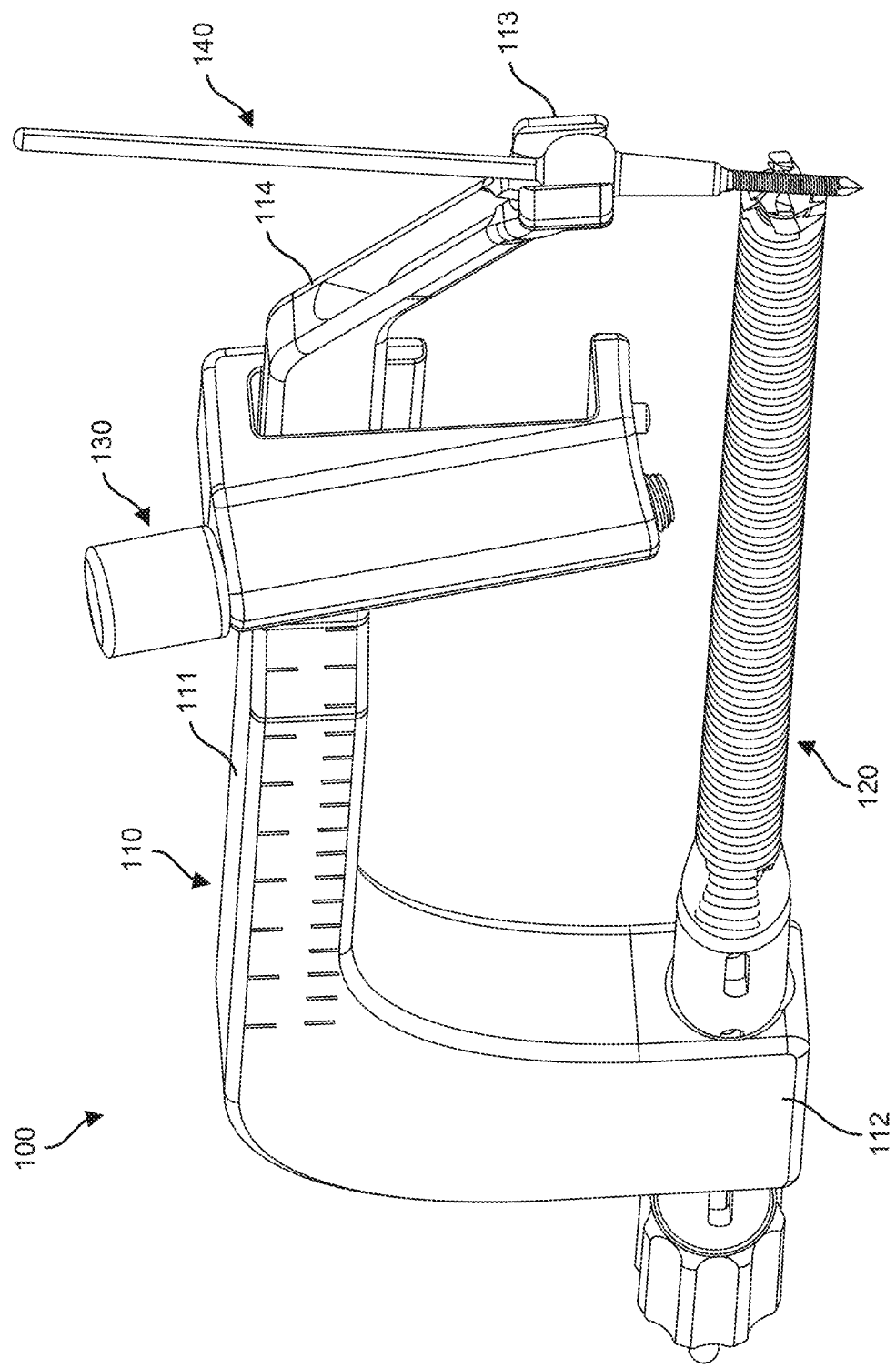
FIG. 2 is a front perspective view of the targeting guide of FIG. 1, in accordance with an aspect of the present invention.
Figure 3:
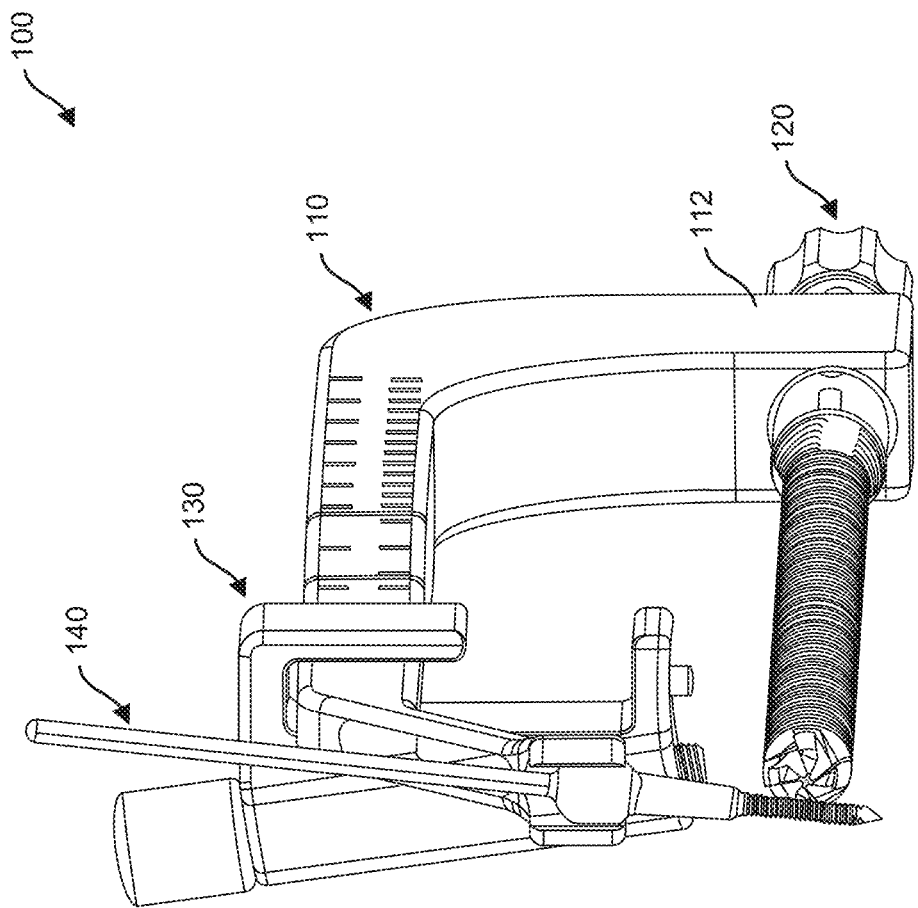
FIG. 3 is a second front perspective view of the targeting guide of FIG. 1, in accordance with an aspect of the present invention.
Figure 4:
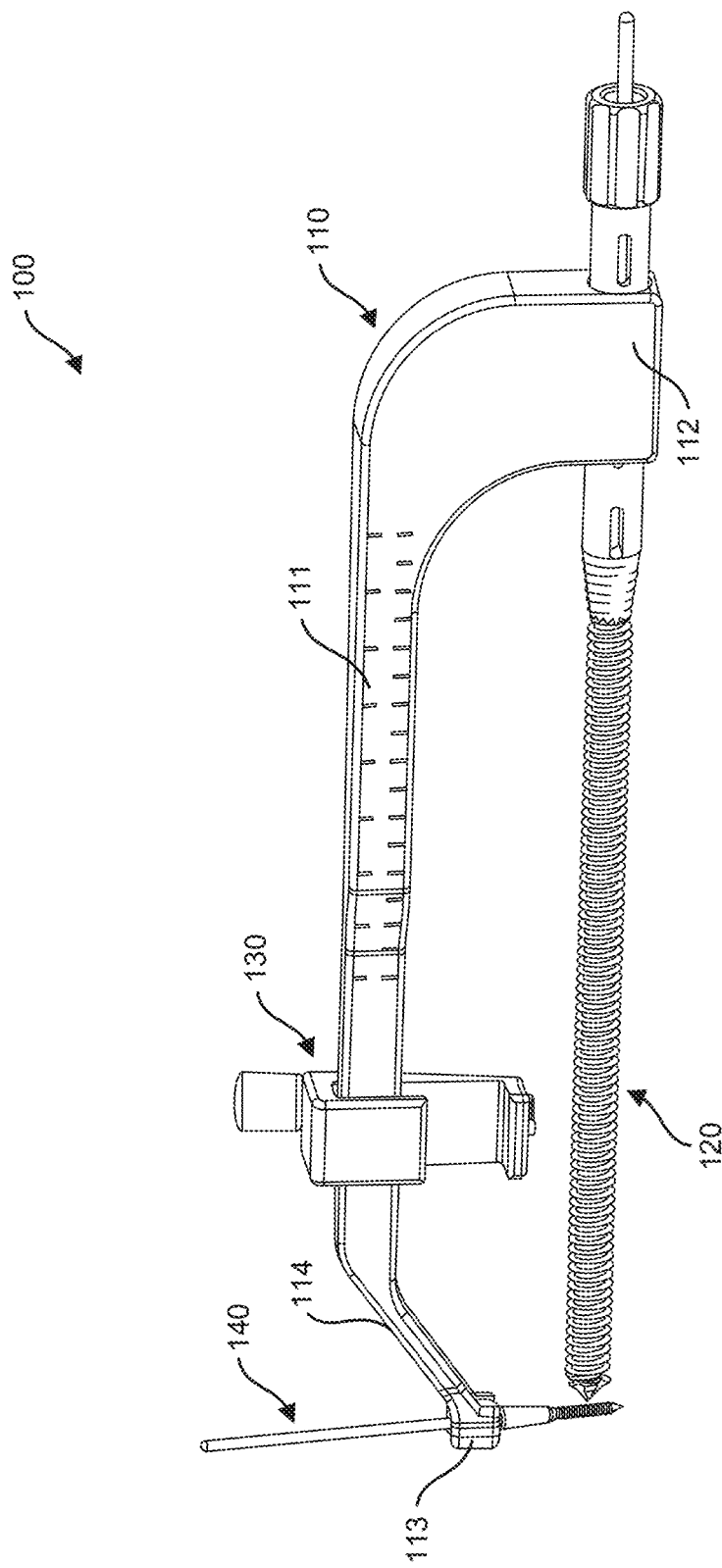
FIG. 4 is a second side perspective view of the targeting guide of FIG. 1, in accordance with an aspect of the present invention.

As seen in FIGS. 1 and 2, the implant holder 130 is placed on the body 111 of the guide arm 110. The implant holder 130 is configured to slide along a top surface of the body 111 to allow for location adjustability. Further, the guide arm 110 includes a second end 113 that is located at the end of an angled portion 114 of the body 111.

The guide arm 110 is shown in FIGS. 6-9, and includes the first end 112 that is connected to a second end 113 by the elongate body 111. The first end 112 may, for example, include a wider portion 115 that includes arcuate sides that may attach the wider portion 115 in a generally perpendicular direction relative to the body 111. The wider portion 115 also includes the through hole 116 that is sized to receive the target member 120. It would be understood by one skilled in the art that the hole 116 may be smaller and/or larger than as shown in FIGS. 6-9 as the hole dimension will depend upon the size and configuration of the target member 120 that is used. The hole 116 is oriented in a direction to allow the target member 120 to extend parallel to the body 111 of the guide arm 110.

Figure 6:
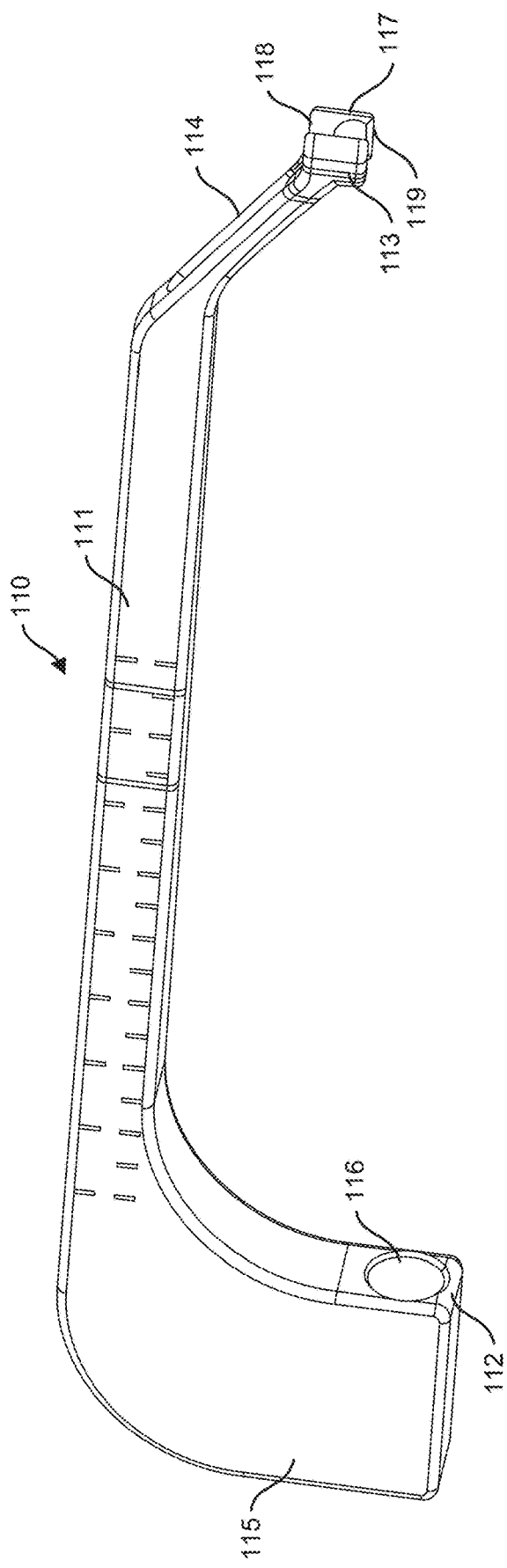
FIG. 6 is a side perspective view of the guide arm, in accordance with an aspect of the present invention.
Figure 7:
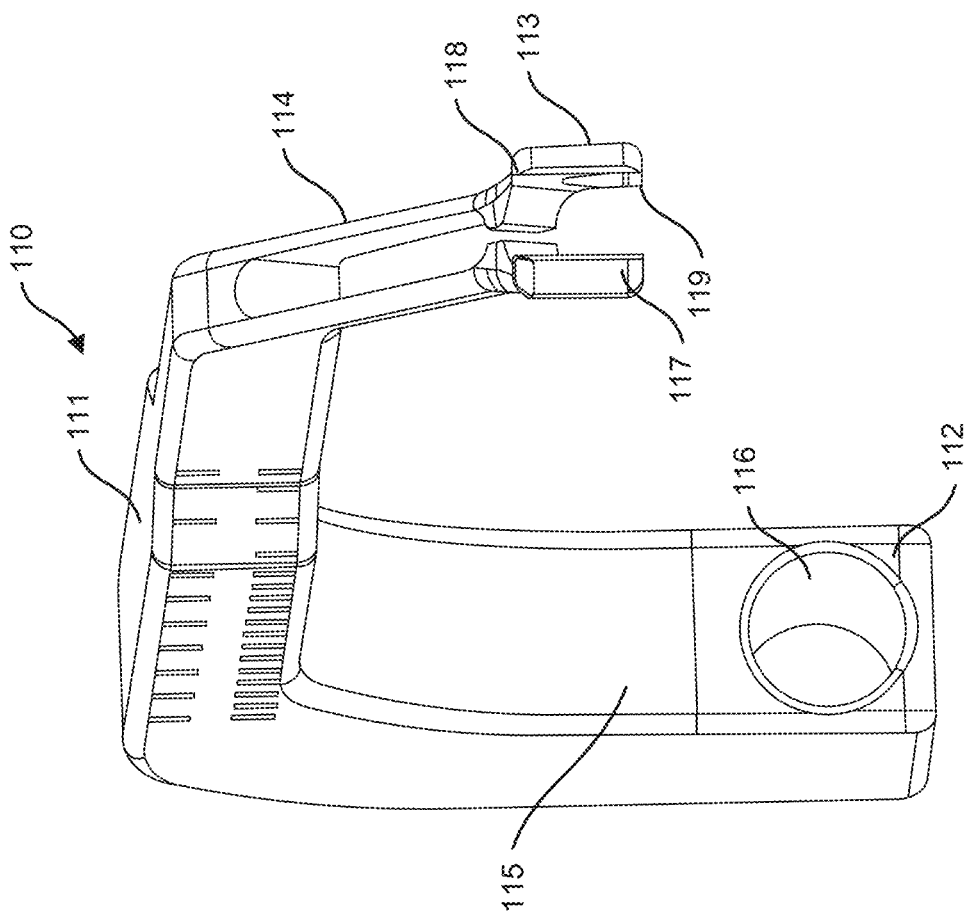
FIG. 7 is a front end perspective view of the guide arm of FIG. 6, in accordance with an aspect of the present invention.
Figure 8:
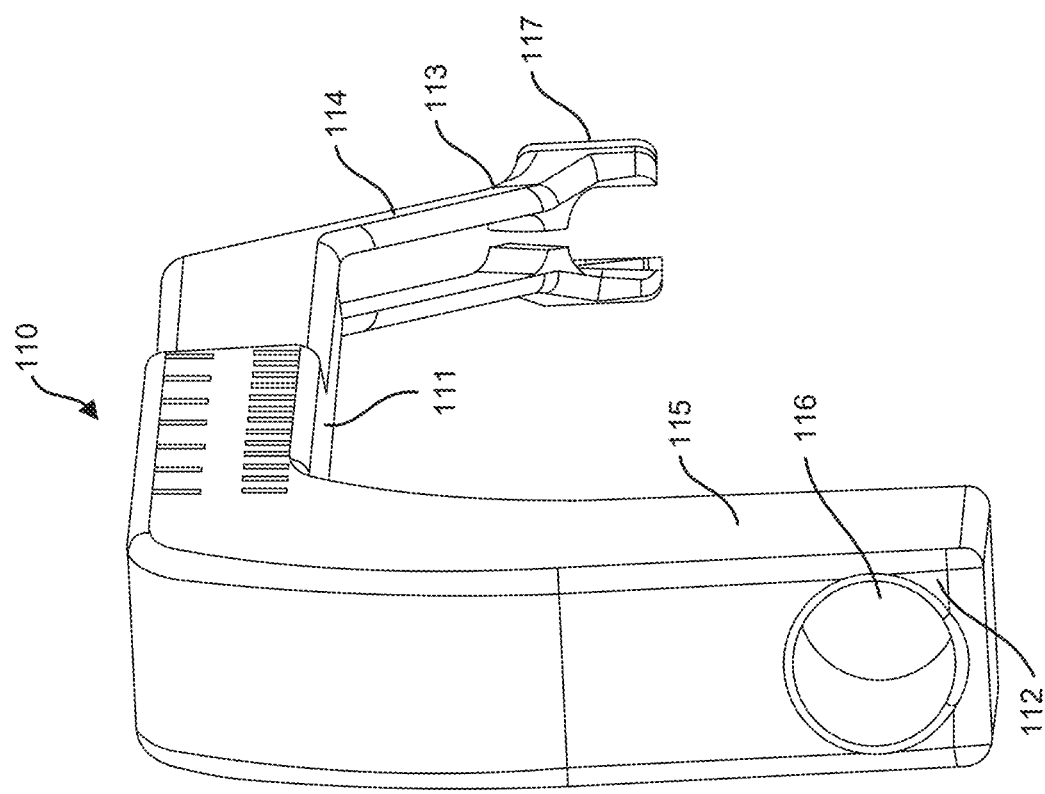
FIG. 8 is a back end perspective view of the guide arm of FIG. 6, in accordance with an aspect of the present invention.
Figure 9:
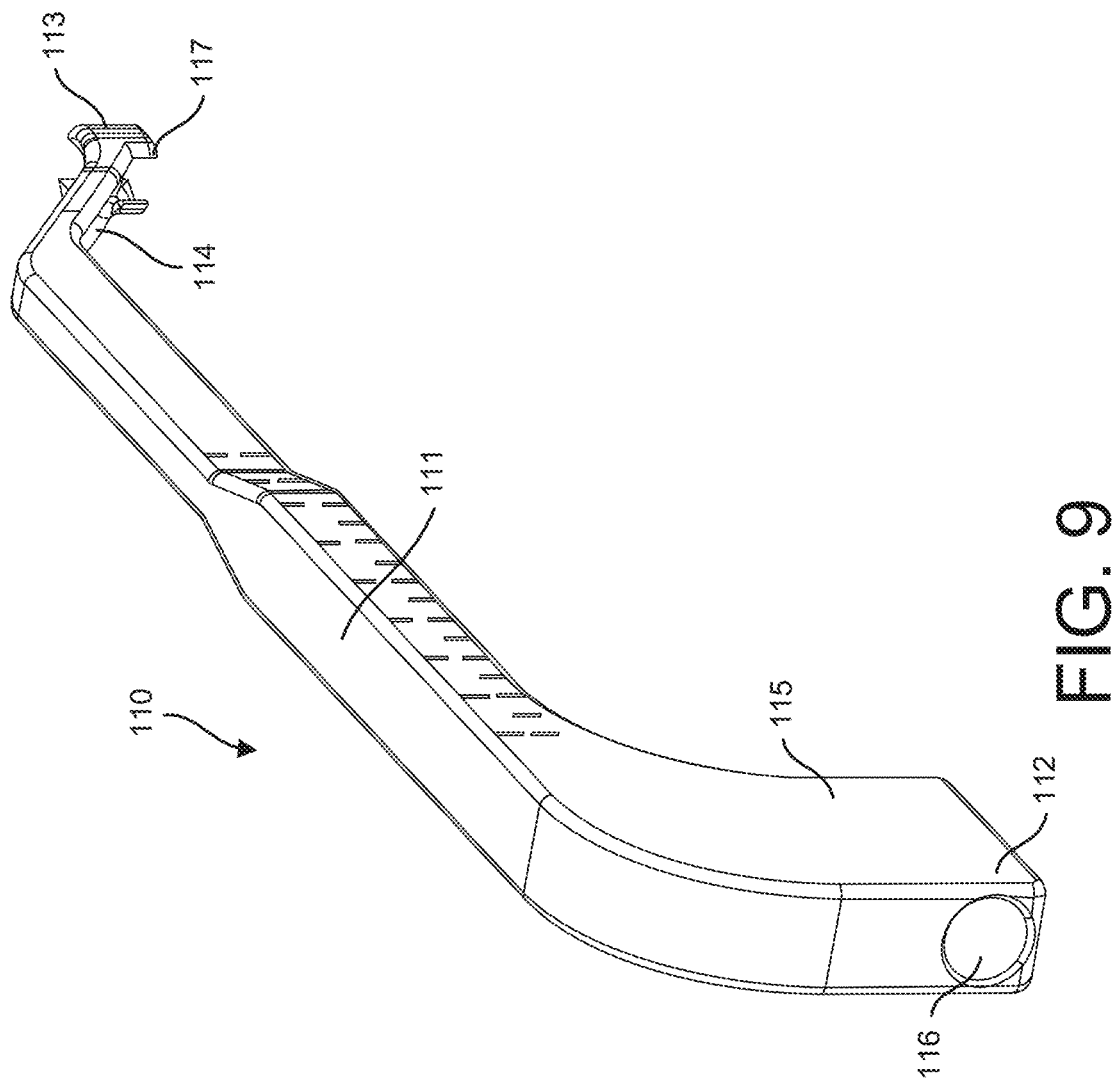
FIG. 9 is a top perspective view of the guide arm of FIG. 6, in accordance with an aspect of the present invention.
Figure 14:
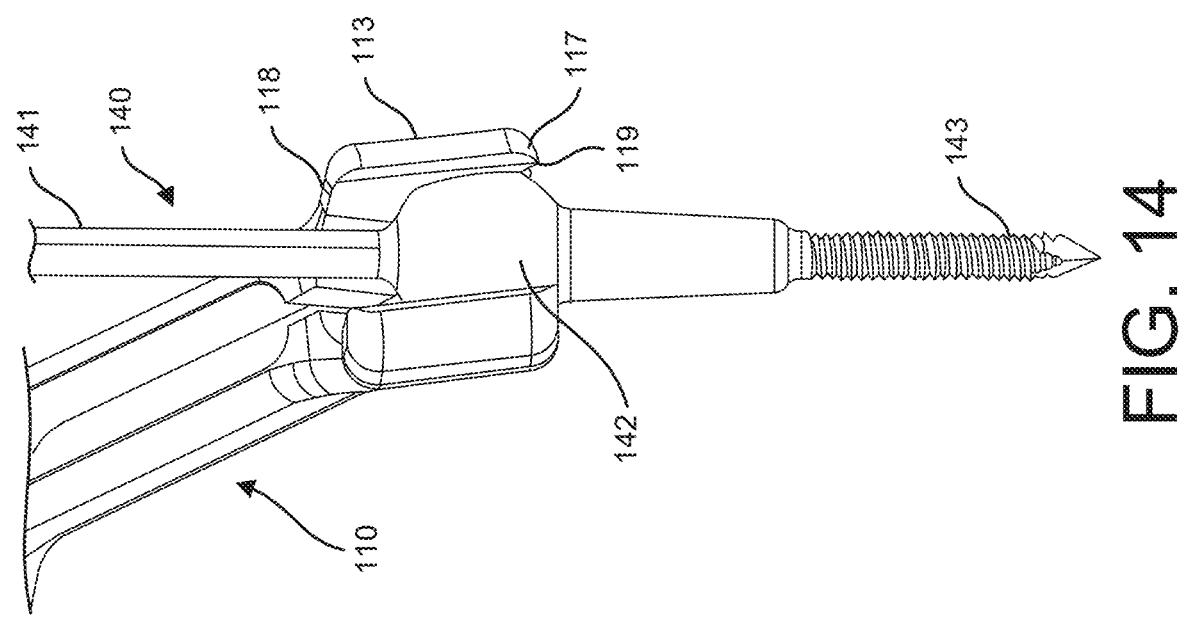
FIG. 14 is an enlarged view of the pivot end of the guide arm with the inserted guide pin, in accordance with an aspect of the present invention.

The angled portion 114 extends in a downward angled direction from the body 111 to the second end 113. Positioned at the second end 113 is a housing element 117 that is configured to receive the guide pin 140. As seen in FIGS. 6, 7, and 14, the housing element 117 includes an inner surface that is configured or sized and shaped to allow the guide pin 140 to pivot, rotate or move in multiple planes. FIG. 14 also shows that housing element 117 has a top opening 118 that is sized to allow for the insertion of the guide pin 140. The bottom opening 119 may be slightly smaller than the top opening 118 to capture and/or retain the guide pin 140 within the inner cavity of the housing element 117.

Figure 12:
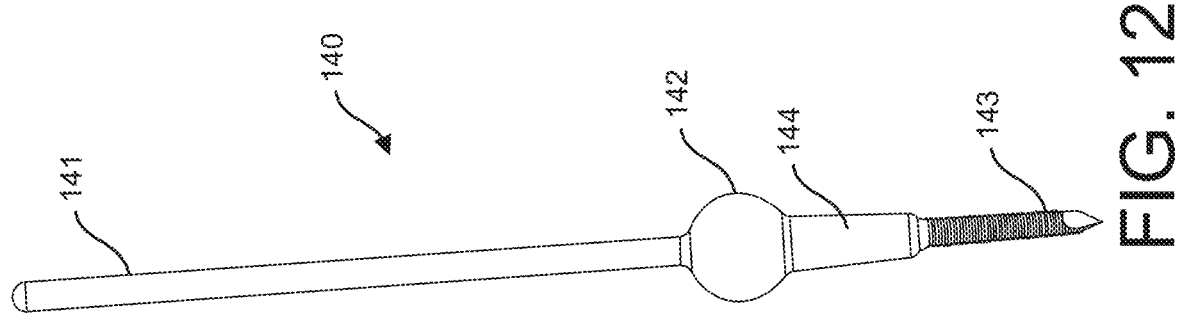
FIG. 12 is a side view of the guide pin, in accordance with an aspect of the present invention.
Figure 13:
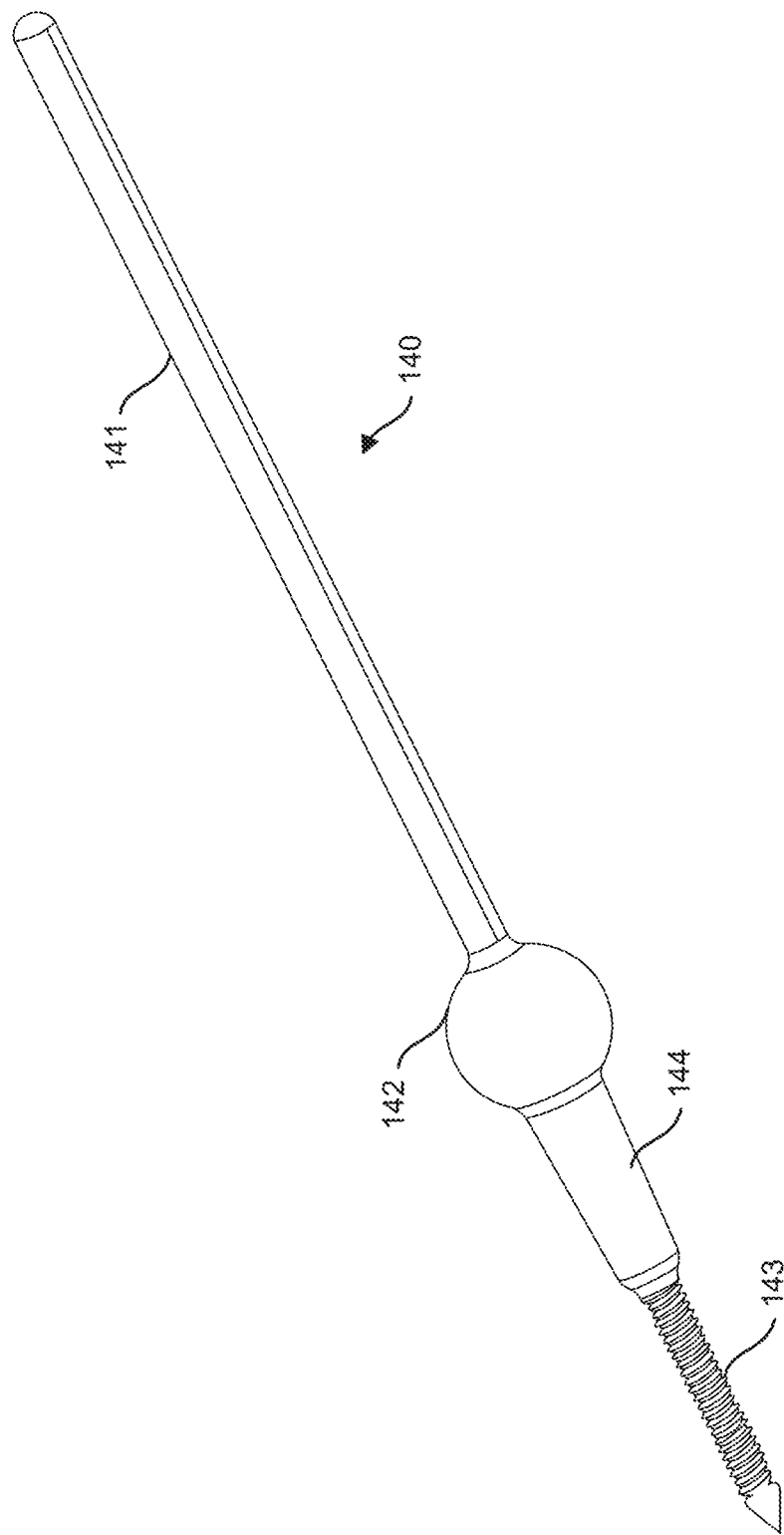
FIG. 13 is a side perspective view of the guide pin of FIG. 12, in accordance with an aspect of the present invention.

FIGS. 12-13 show an embodiment of the guide pin 140 that may be inserted in the housing element 117. The guide pin 140 includes a shaft 141, a sphere 142, a tip 143 and a tapered portion 144. The tip as shown in FIG. 12 is threaded, however, it is also contemplated that the tip may have a smooth outer surface to facilitate insertion. The sphere 142 is sized and shaped or configured to be inserted into the housing element 117, as shown in FIG. 14, to allow for a full range of pivoting motions, when in use. The tip 143 is configured or sized and shaped to allow for the user to insert the guide pin 140 into a target bone either directly or through the skin and then be secured therein to establish the target location for the elongated target member 120.

With continued reference to FIGS. 12-13, the tapered portion 144 of the shaft 141 has a larger diameter proximate to the sphere 142 and then tapers down to a smaller diameter proximate to the tip 143. The tapered portion 144 functions to prevent the guide pin 140 from plunging or being inserted too deep into the target bone. The tapered portion 144 also may operate to ensure accurate positioning of the guide pin 140 to accomplish precise targeting functionality of the targeting guide 100.

Although not shown, the second end 113 may have an alternative configuration which may include, for example, a universal joint, hinged joint or other constrained mobile connection that could be utilized in place of the spherical guide pin 140—housing element 117 assembly. The housing element 117 may include, for example, a movable joint construct through which a guide pin, Steinman pin, K-wire or other elongated member is connected and used to establish a target location in vivo.

Figure 10:
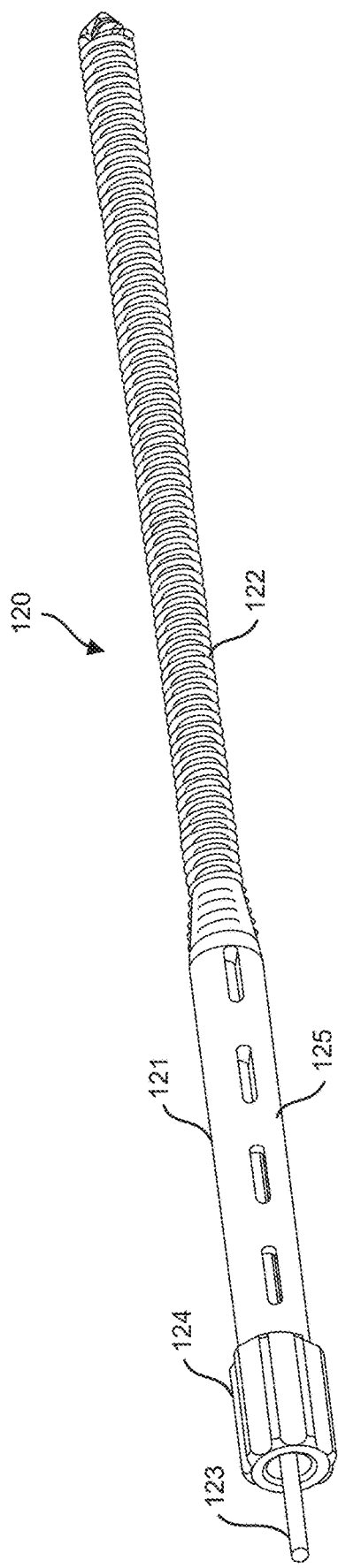
FIG. 10 is a side perspective view of the target member, in accordance with an aspect of the present invention.
Figure 11:
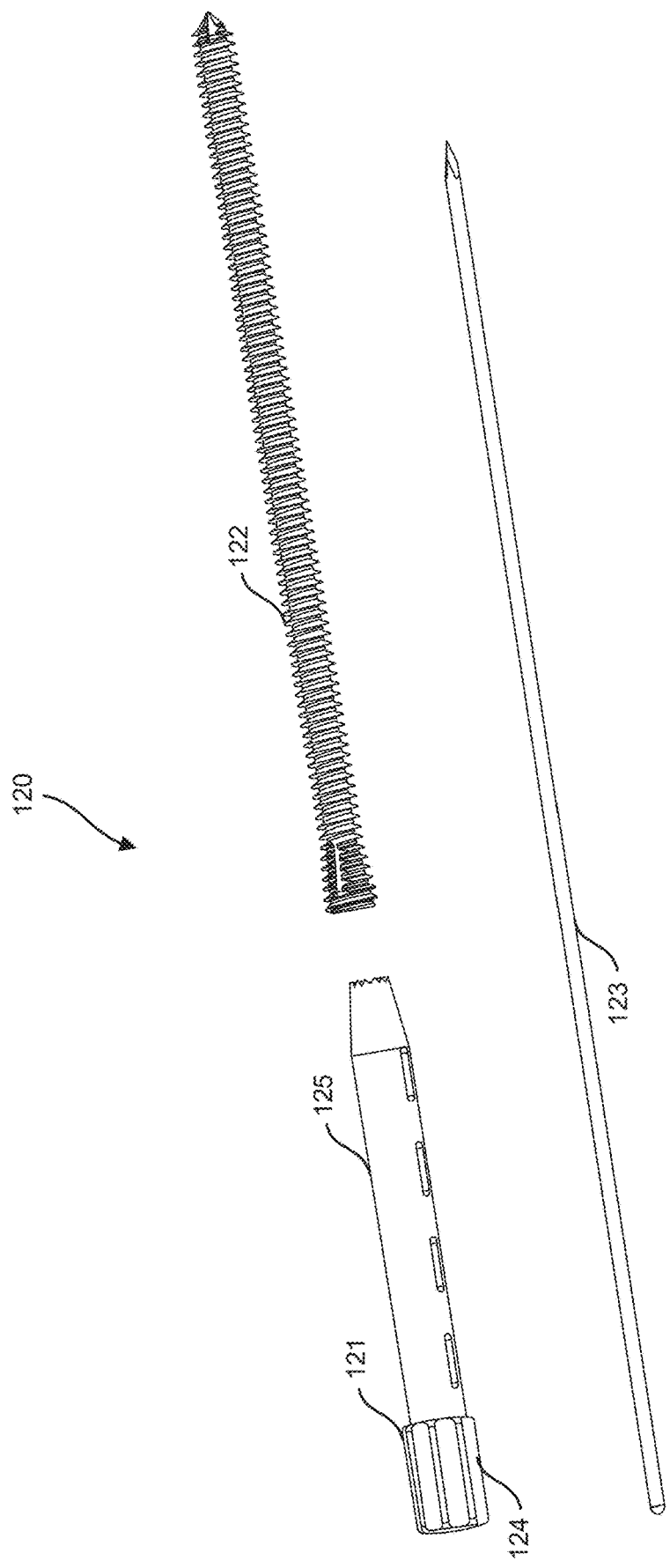
FIG. 11 is an exploded view of the target member of FIG. 10, in accordance with an aspect of the present invention.

Referring now to FIGS. 10-11, a target member 120 is shown. The target member 120 includes, for example, a three piece construct with a protector member 121, a threaded member 122 and a target pin 123. The protector member 121 has a knob 124 and a cylindrical portion 125 that are cannulated and can be coupled together. The protector member 121 functions to protect the surrounding soft tissue when the target pin 123 is inserted. As shown in FIG. 11, the threaded member 122 may have one end that is tapered to facilitate insertion and placement in vivo. The opposite end of the tube-like structure of the threaded member 122 has cutting flutes to facilitate the insertion of the target member into bone. The threaded member 122 may be cannulated or alternatively, be solid with no longitudinal opening. The threaded member 122, as seen in FIGS. 10 and 11, is threaded along its entire length, however, one skilled in the art would contemplate using partially or segmentally divided threads depending on the clinical application. The third piece of the target member 120 is an elongated pin like structure 123. The elongated pin like structure 123 may be, for example, a target pin, guide wire, k-wire or the like. The target pin 123 as shown, may have, for example, a smooth outer surface with a one sharpened end. When in use, typically the target pin 123 is inserted first from a distal to proximal direction with the pin 123 passing through the cannulated passage of the protector member 121 and threaded member 122 when this construct is being threaded into a bone pathway to secure the targeting guide in the surgical site and allow for the establishment of a target location proximally. The fully assembled targeting guide 100 is shown in FIGS. 1-4 with the target member 120 in place.

Figure 5:
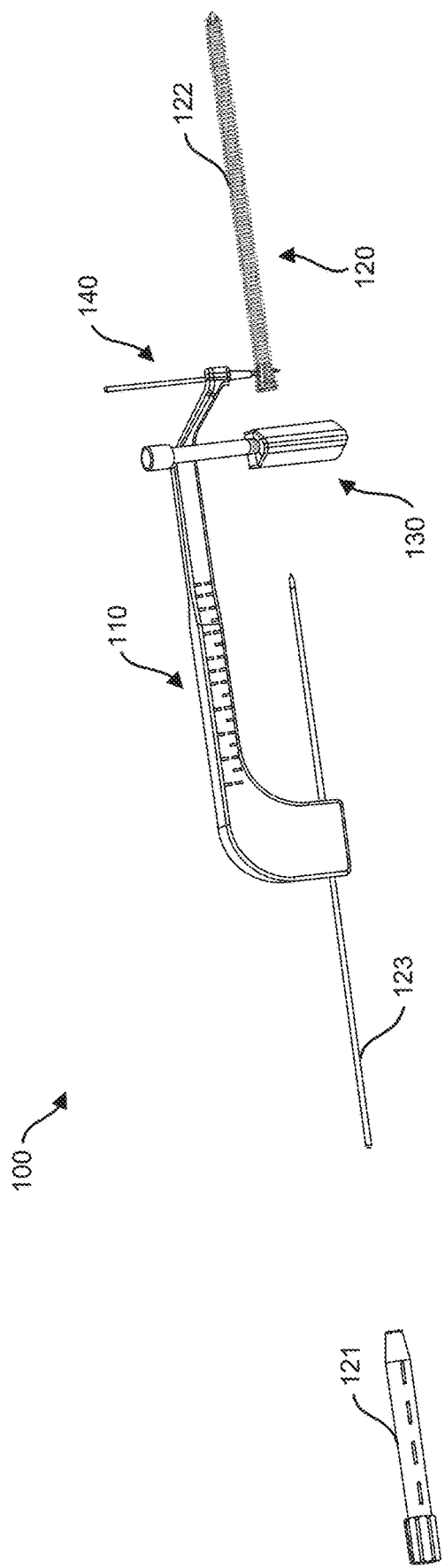
FIG. 5 is an exploded view of the targeting guide of FIG. 1, in accordance with an aspect of the present invention.

Further, FIG. 5 shows an exploded view of the targeting guide 100 and the disassembled target member 120. It will be understood by one of ordinary skill in the art that the target member 120 shown is one embodiment and that other constructs are also contemplated, for example, a one piece rod like structure, with or without threads, or alternatively, a two piece structure that includes threaded and non-threaded elements.

Figure 15:
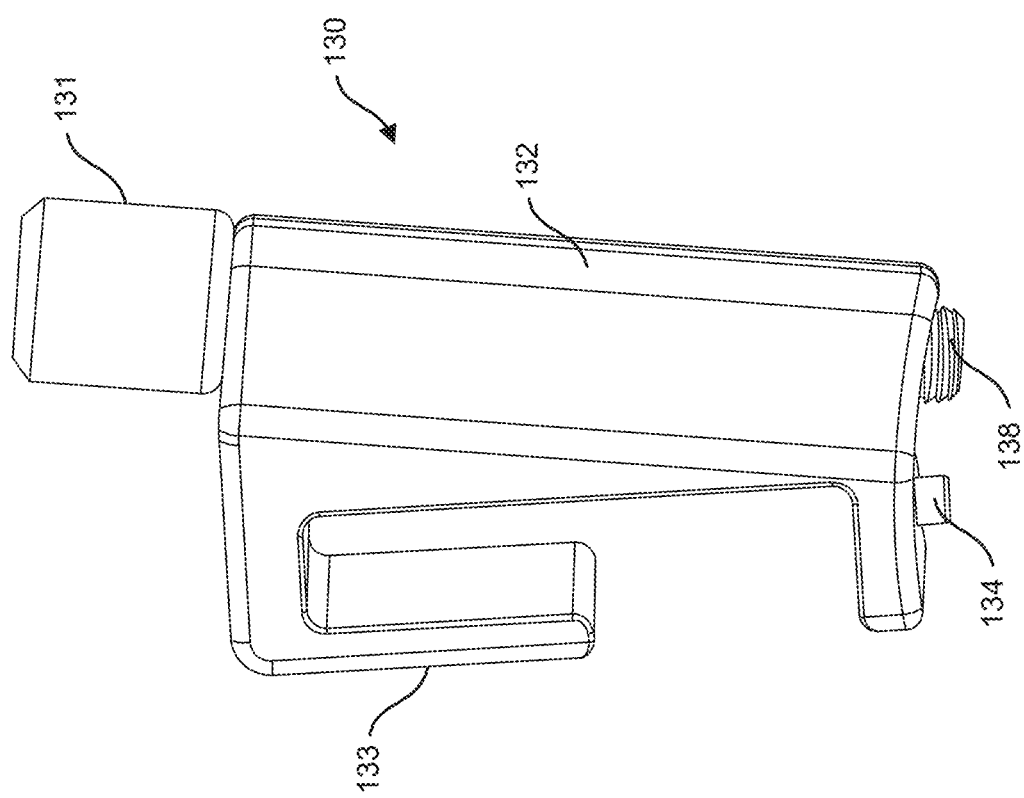
FIG. 15 is a side perspective view of the implant holder, in accordance with an aspect of the present invention.
Figure 16:
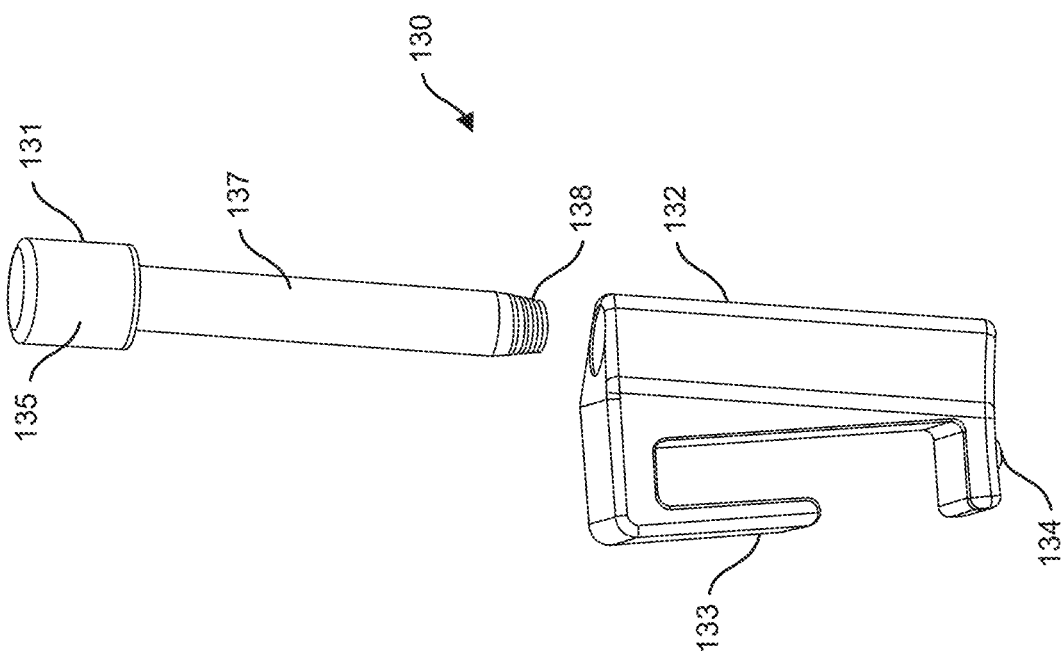
FIG. 16 is an exploded view of the implant holder of FIG. 15, in accordance with an aspect of the present invention.
Figure 17:
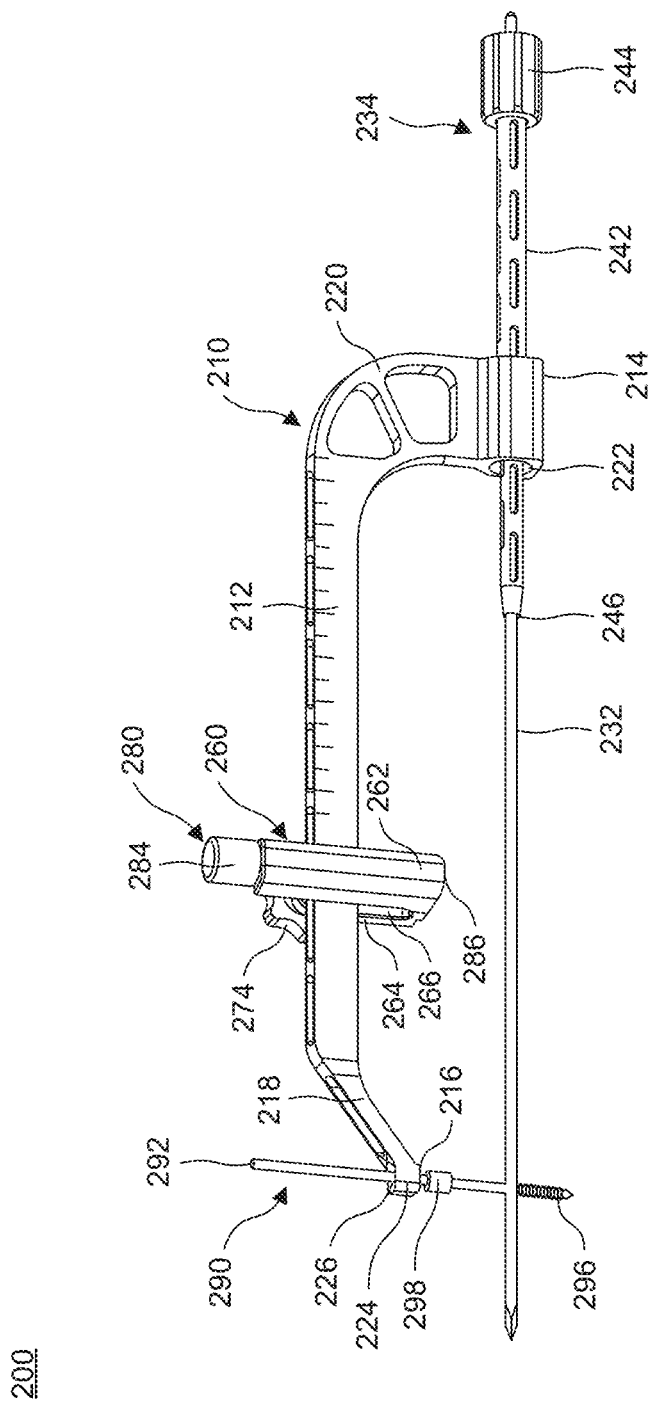
FIG. 17 is a first perspective, side view of a portion of another targeting guide system with a protector member, in accordance with an aspect of the present invention.
Figure 18:
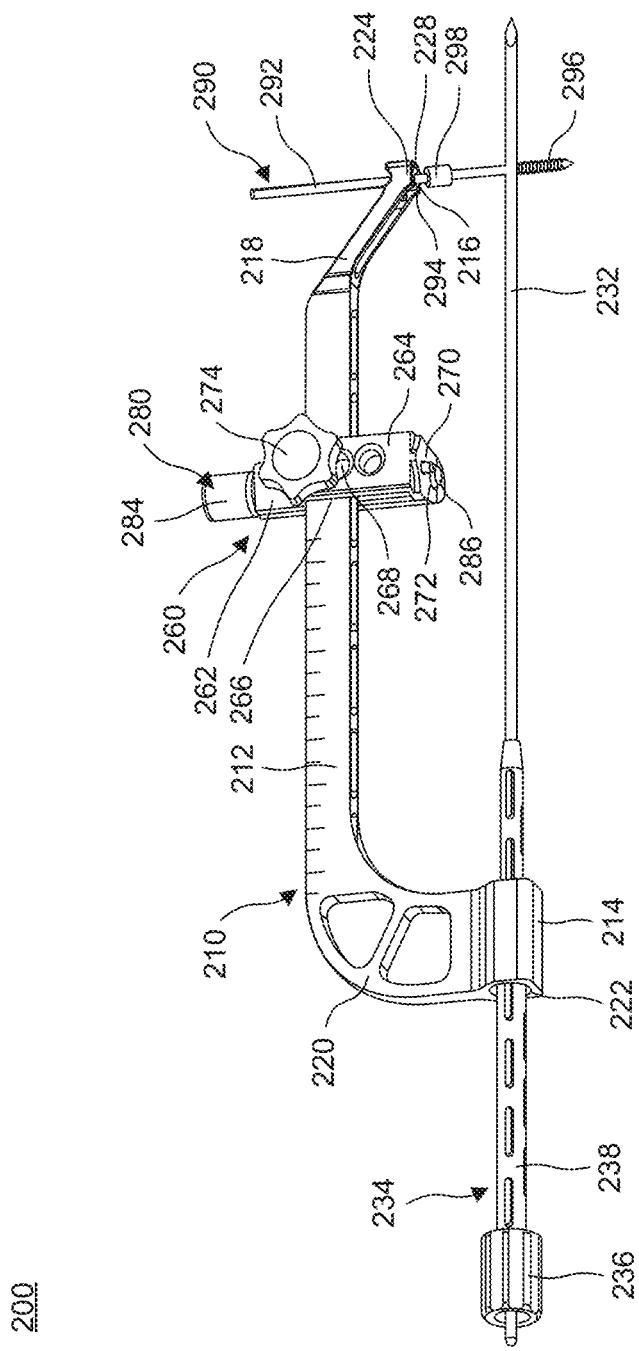
FIG. 18 is a second perspective, side view of the portion of the targeting guide system of FIG. 17, in accordance with an aspect of the present invention.
Figure 19:
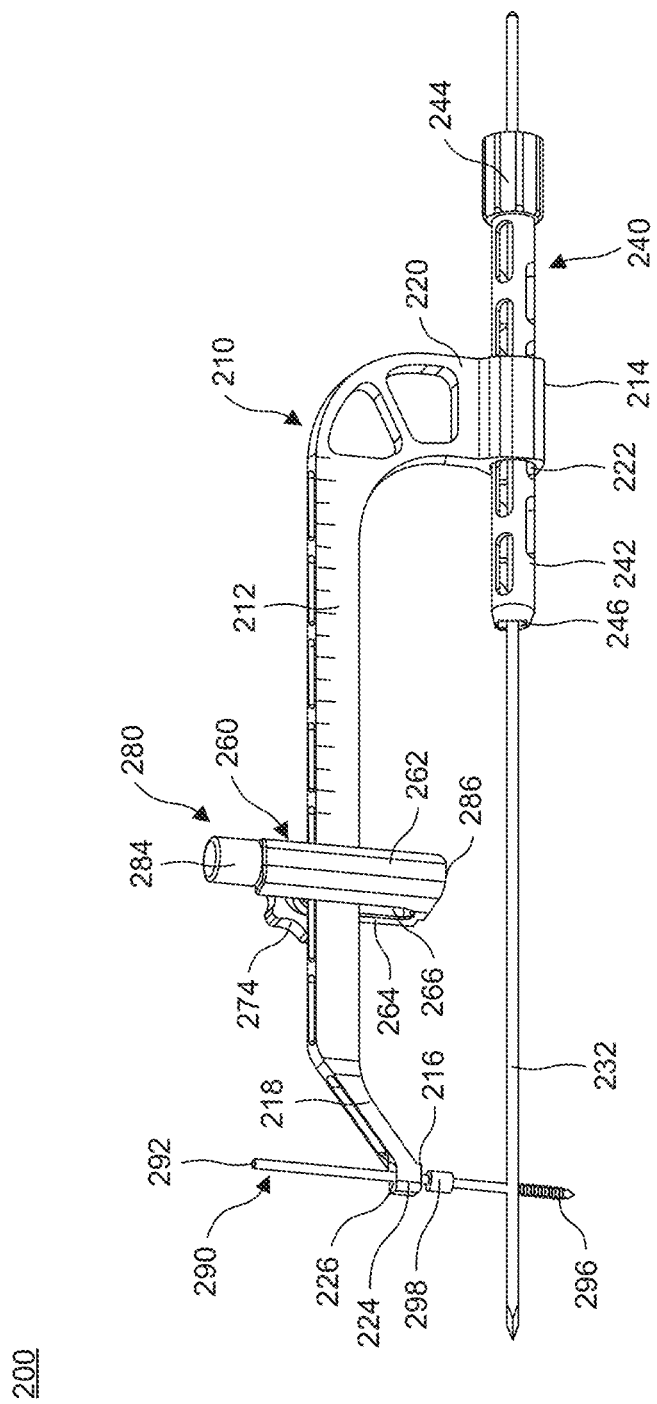
FIG. 19 is a first perspective, side view of the targeting guide system of FIG. 17 with the protector member replaced with a drill guide, in accordance with an aspect of the present invention.
Figure 20:
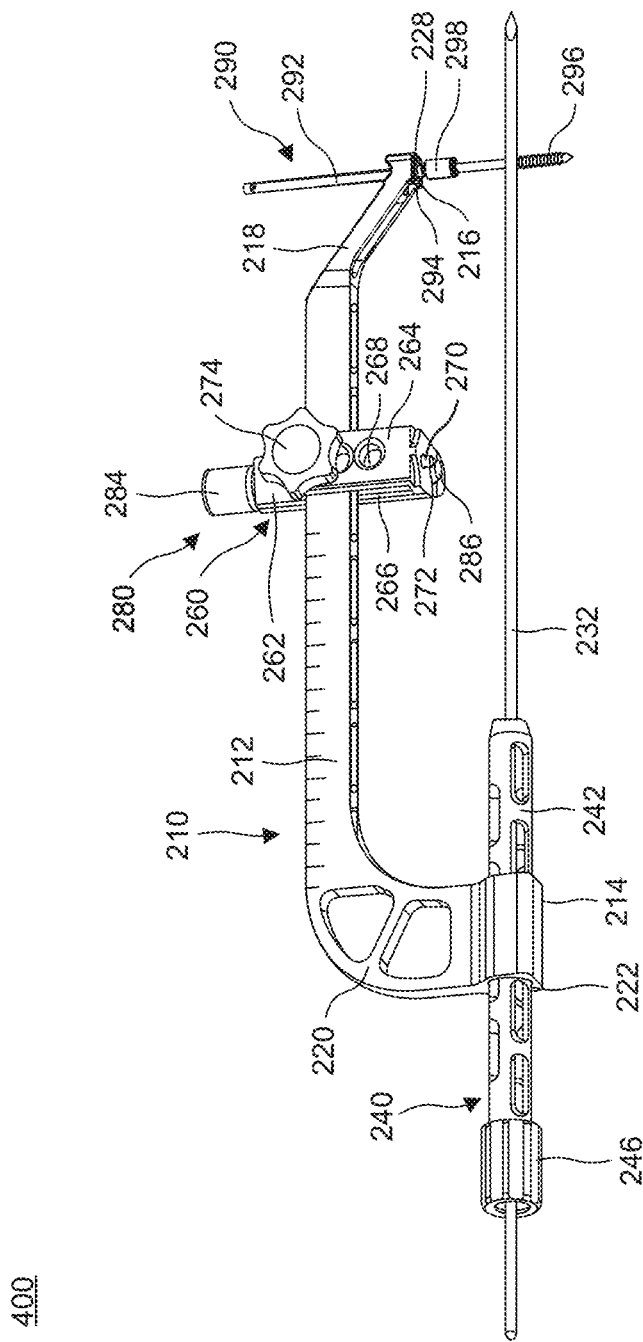
FIG. 20 is a second perspective, side view of the targeting guide system of FIG. 19, in accordance with an aspect of the present invention.
Figure 21:
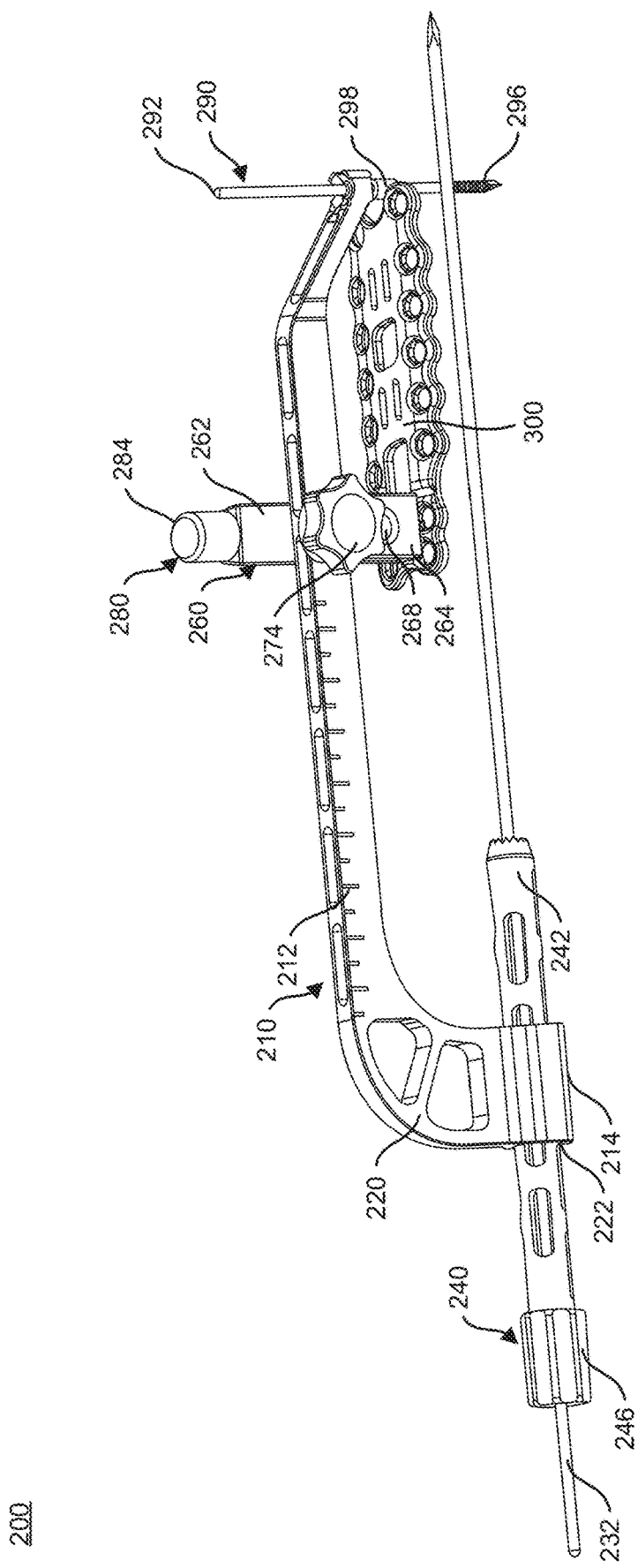
FIG. 21 is a perspective view of the targeting guide system of FIG. 19 with a bone plate attached, in accordance with an aspect of the present invention.
Figure 22:
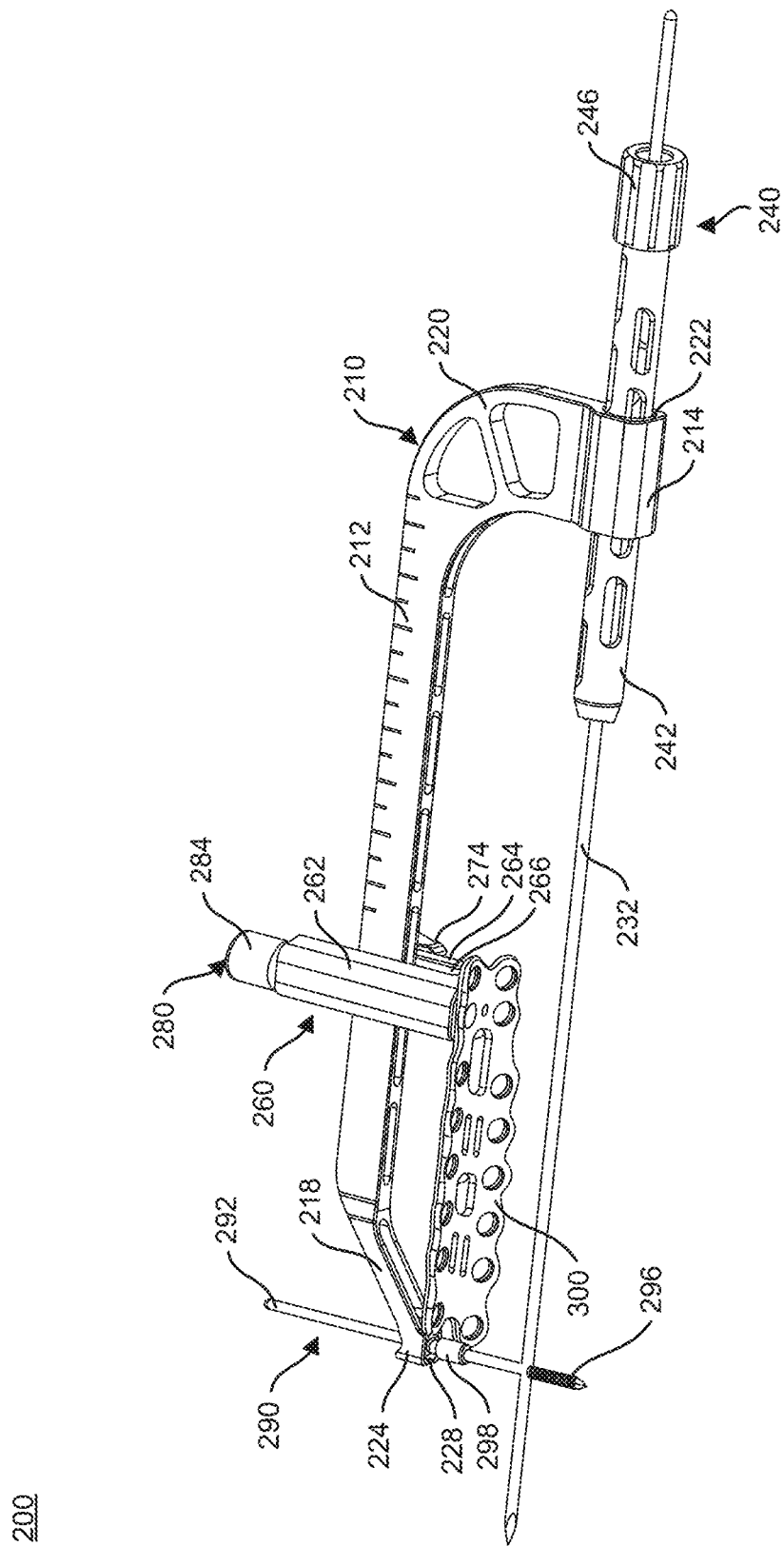
FIG. 22 is another perspective view of the targeting guide system of FIG. 21, in accordance with an aspect of the present invention.
Figure 23:
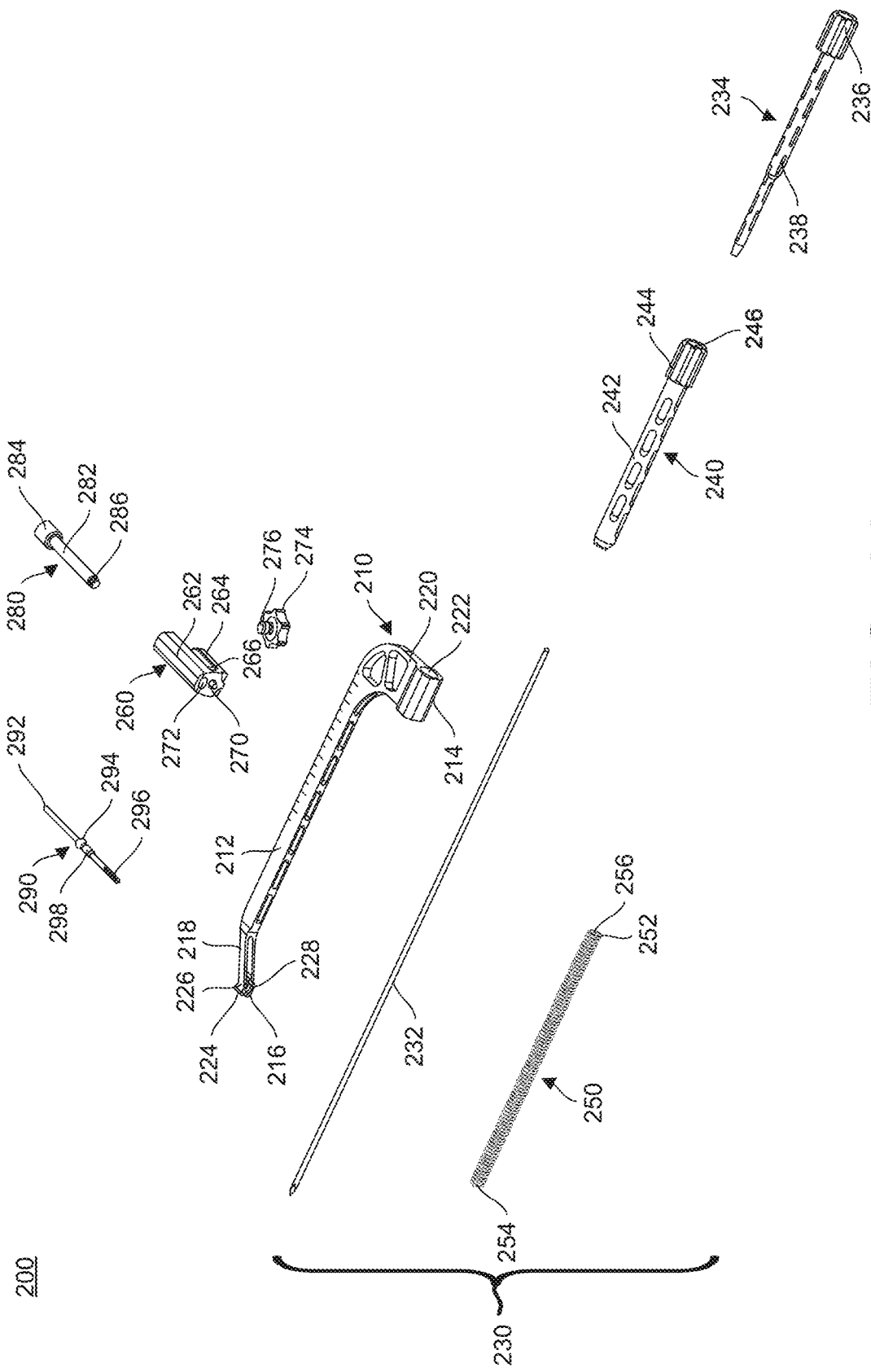
FIG. 23 is an exploded perspective view of the complete targeting guide system of FIG. 17, in accordance with an aspect of the present invention.
Figure 24:
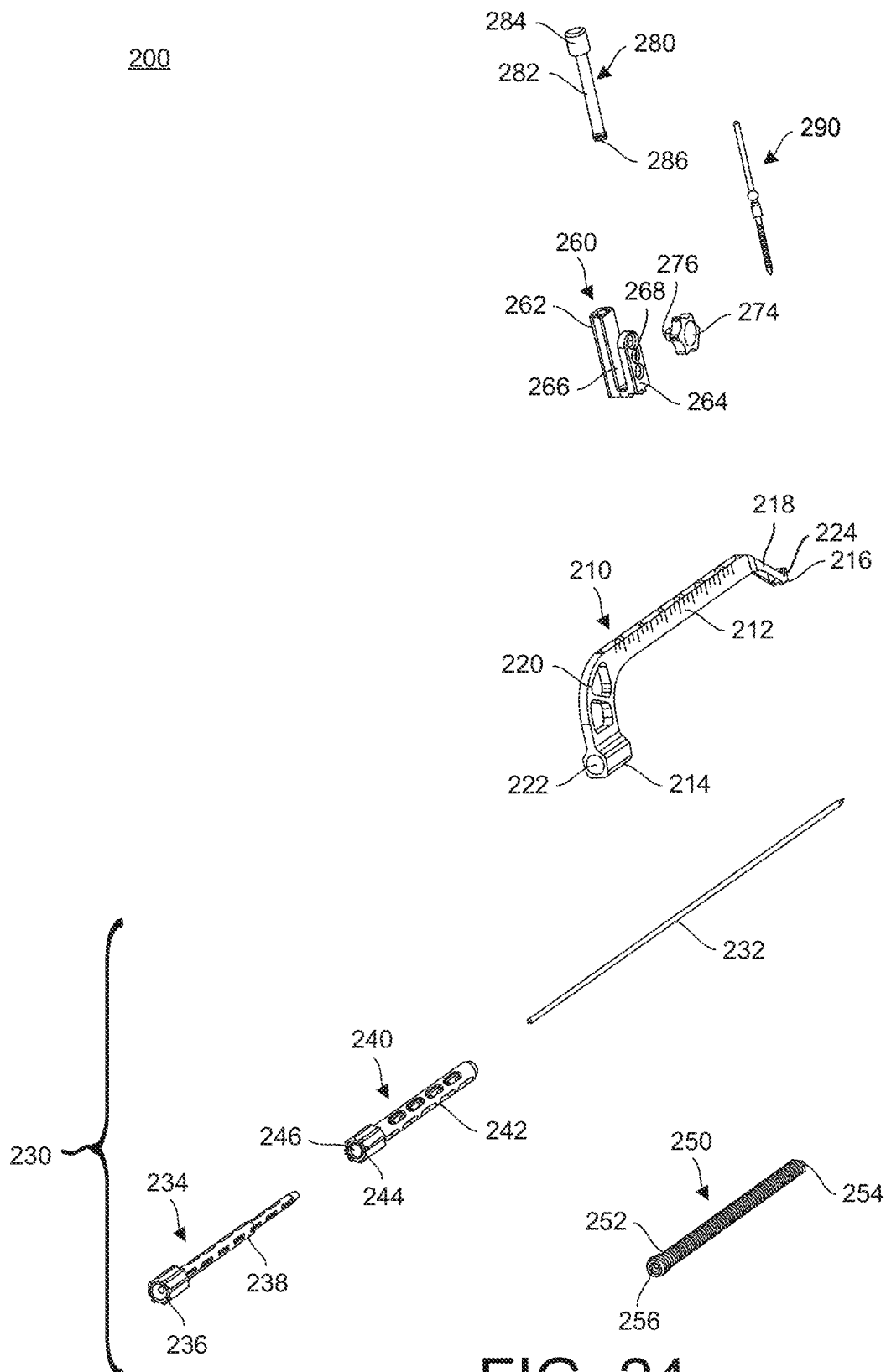
FIG. 24 is another exploded, perspective view of the targeting guide system of FIG. 23, in accordance with an aspect of the present invention.
Figure 25:
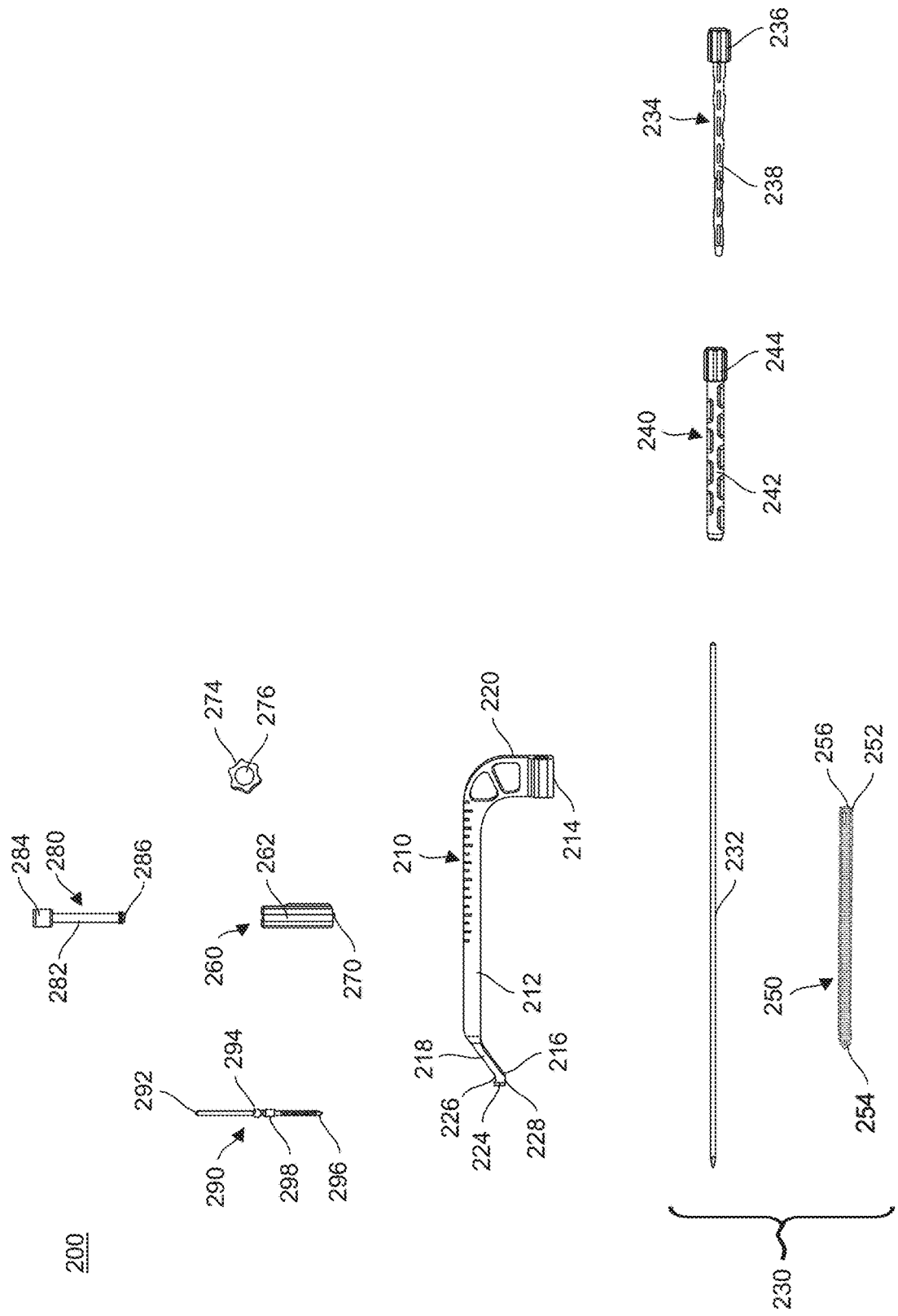
FIG. 25 is an exploded, first side view of the targeting guide system of FIG. 23, in accordance with an aspect of the present invention.
Figure 26:
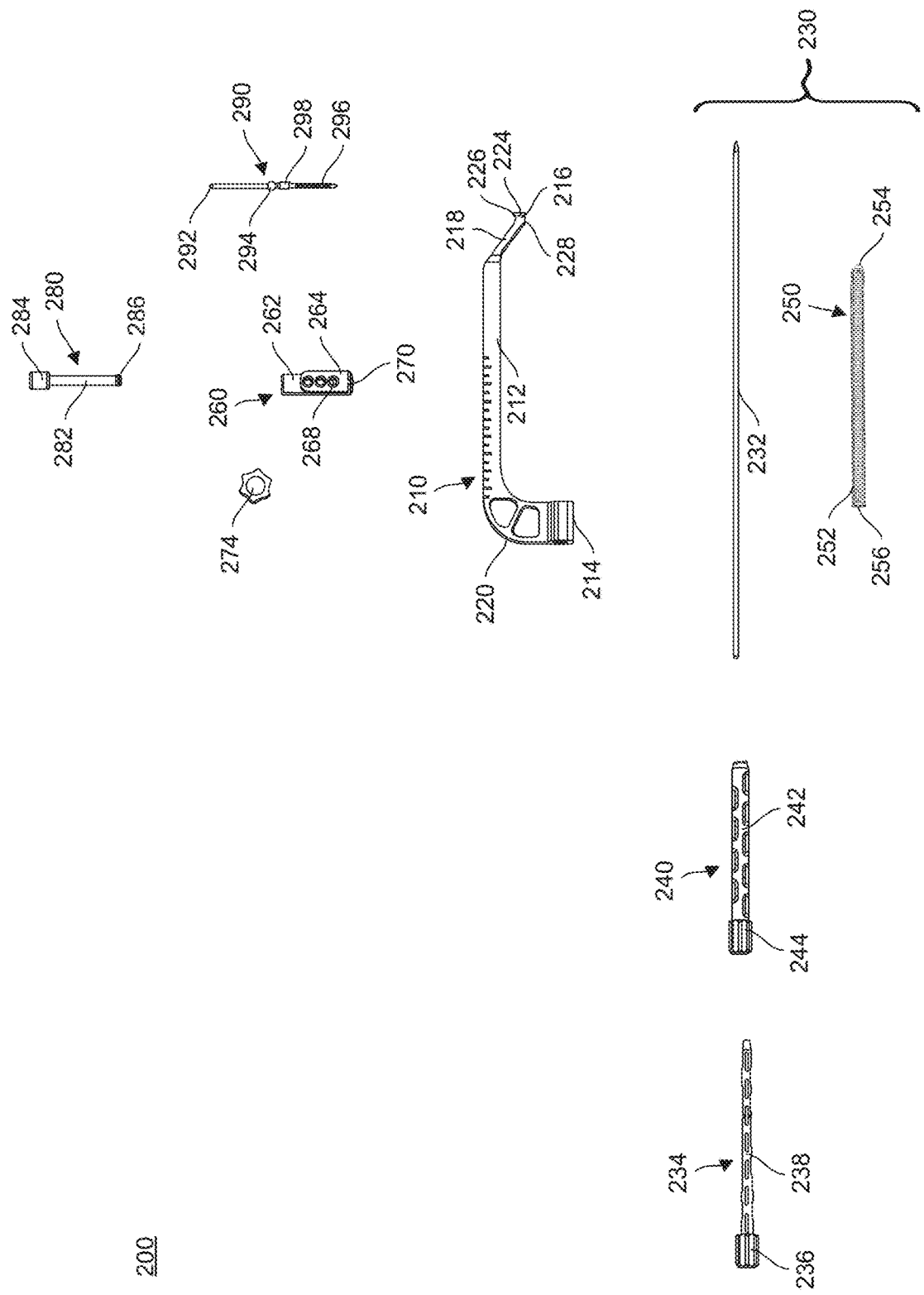
FIG. 26 is an exploded, second side view of the targeting guide system of FIG. 23, in accordance with an aspect of the present invention.

Referring now to FIGS. 1-4 and 15-16 the implant holder is shown. The implant holder may be detachably attached to the body 111 of the guide arm 110. The implant holder 130 includes a locking member 131, a housing 132, an attachment arm 133 and an alignment post 134. The locking member 131 is positioned in a hole that has an opening at the top surface of the housing 132 and exits through an opening on the bottom surface of the housing 132. The locking member 131 includes a knob 135 that allows the user to turn the locking member 131, a shaft 137 that is connected to the knob 135, and a threaded portion 138 of the shaft 137 is positioned at the opposite end of the knob 135. As seen in FIG. 15, when assembled, the shaft 137 of the locking member 131 is wholly contained within the housing as it passes through a through hole in the housing 132. The implant holder 130 also has an alignment post 134 that is adjacent to the threaded portion 138. The implant holder 130 further has an attachment arm 133 that is generally configured as a hook like structure. The attachment arm 133 hooks over the top of the body 111 of the guide arm 110 to permit the sliding movement along the longitudinal axis of the body 111, as shown in FIGS. 1-4. The threaded portion 138 of the implant holder 130 may be, for example, secured to a bone plate. The threaded portion 138 may be threaded into a corresponding hole in the plate and the alignment post 134 is positioned within a second hole in the surface of the plate to secure the plate to the implant holder 130 and allow the user to move the secured implant along the length of the body 111.

A surgical method for correcting bone deformities using the targeting guide instrument of FIGS. 1-16 is disclosed. The method includes, for example, performing an arthrodesis across a minimum of one joint. A minimum of two bones are positioned in their desired final position and can be fixed temporarily via various means. The guide pin 140 sets the trajectory for the target pin 123 and the threaded member 122. The method includes further the placing of the guide pin 140 in a bone such that the trajectory of the target pin 123 will triangulate to the threaded portion 143 of the guide pin 140. The configuration of the guide arm 110 may provide guidance as to the location along the threaded portion 143 of the guide pin 140 where the target pin 123 will aim. The guide arm 110 may be adjusted for bones where the user may want to place the guide pin 140 deeper to allow for better fixation, while aiming closer to the edge or cortical surface of the bone. Next, the method may include attaching the housing element 117 of the guide arm 110 to the sphere 142 of the guide pin 140. Further, the method may include placing the protector member 121 in the hole 116. A target pin 123 may be placed into the protector member 121 and inserted past at least two bones but may be inserted to or past the threaded portion 143 of the guide pin 140. The method may include removing the protector member 121 by sliding it out of the guide arm 110. The guide arm 110 is removed from the sphere 142 of the guide pin 140. The guide pin 140 may also be removed at this time or can be removed at a later time. A cannulated drill may be used to drill over the target pin 123. The threaded member 122 is then inserted over the target pin 123 to the desired depth. Alternatively, if the threaded member 122 is not cannulated, the target pin 123 can be removed and the threaded member 122 inserted through the drill hole.

In one embodiment, the method may also include using an implant holder 130. The implant holder 130 is attached to an implant (not shown). The implant may be, for example, a bone plate. The implant holder 130 may be attached to the guide arm 110 prior to placement on the guide pin 140, or can be placed after the guide arm 110 is placed on the guide pin 140. Likewise, the implant may be attached to the implant holder 130 prior to placement on the guide arm 110 or may be pre-assembled and then the implant holder 130 is attached to the guide arm 110. The implant position may be adjusted along the length of the guide arm 110 to allow for implant positioning along a first plane. For example, along the sagittal plane. Alternatively, the guide arm 110 can be rotated around the guide pin 140 to rotate the plate in a second plane, for example the frontal plane. Movement of the implant in these two planes allows for fixation devices to be inserted with a trajectory to avoid contacting the threaded member 122. The implant may secured with locking or non-locking fixation devices prior to placement of the guide pin 140. Alternatively, the implant may be secured after the placement of the guide pin 140.

A method of assembling the targeting guide 100 includes obtaining a guide arm 110 and a guide pin 140. Placing the guide pin 140 in a bone. The method may further include attaching the guide arm 110 to the guide pin 140 at the second end 113 and inserting the protection member 121 into the hole 116. Further, the method may include inserting the target pin 123 through the protection member 121 and then removing the protection member 121 from the hole 116.

Referring now to FIGS. 17-31, another targeting guide assembly 200 is shown. The targeting guide assembly 200 includes a guide arm 210, a target member 230, an implant holder 260, and a guide pin 290. The target member 230 is received within a first end of the guide arm 210. The implant holder 260 moveably engages the guide arm 210 and may, for example, slide along a top surface of a body 212 of the guide arm 210 to allow for location adjustability of a bone plate 300, as shown in FIGS. 28 and 29. The guide pin 290 rotatably couples to the second end of the guide arm 210. The implant holder 260 couples to a bone plate 300.

As shown in FIGS. 17-26, the guide arm 210 includes a body 212 connecting a first end 214 and a second end 216 of the guide arm 210. The first end 214 may, for example, include a wider portion 220 that includes arcuate sides that may attach the wider portion 220 in a generally perpendicular direction relative to the body 212. The wider portion 220 may also include a through hole 222 that is sized and shaped to receive the target member 230. The through hole 222 may be, for example, larger or smaller than as shown in FIGS. 17-26. The through hole 222 may extend through the wider portion 220 parallel to the body 212 allowing the target member 230 to extend parallel to the body 212 of the guide arm 210. The second end 216 may, for example, include an angled portion 218. The angled portion 218 extends in a downward angled direction from the body 212 to the second end 216. A housing element 224 may be positioned at the second end 216 and be configured or sized and shaped to receive the guide pin 290. The housing element 224 may include a top opening 226 and a bottom opening 228 forming an inner surface or cavity extending between the top opening 226 and the bottom opening 228. The housing element 224 may also include a channel extending from an exterior surface of the housing element 224 into the inner surface. The inner surface may be, for example, configured or sized and shaped to allow the guide pin 290 to pivot, rotate, or move in multiple planes. The top opening 226 may be sized to allow for insertion of a sphere 294 of the guide pin 290 into the housing element 224. The bottom opening 228 may be, for example, slightly smaller than the top opening 226 to capture or retain the guide pin 290 within the inner cavity of the housing element 224.

The target member 230 is shown in FIGS. 17-26 and includes a target pin 232, a protector member 234, a drill guide 240, and a threaded member or implant 250. The target pin 232 may be, for example, a guide wire, k-wire, pin, or the like elongated pin like structure or member for insertion through a joint. In the depicted embodiment the target pin 232 has a smooth outer surface with a point or sharped portion at one end.

The target pin 232 may be, for example, inserted from a distal to proximal direction through the cannulated opening of the protector member 234 when inserted into a bone pathway to secure the targeting guide in the surgical site and allow for the establishment of a target location proximally. The protector member 234 may include a knob 236 at a first end of a cylindrical portion 238. The protector member 234 may also include a through hole or cannulated opening extending through the protector member 234 along a longitudinal axis of the protector member 234. The protector member 234 may, for example, protect the surrounding soft tissue when the target pin 232 is inserted through the protector member 234 and into a patient's bones. The drill guide 240 may include a cylindrical portion 242 and a knob 244 positioned at a first end of the cylindrical portion 242. The cylindrical portion 242 of the drill guide 240 may have, for example, a larger diameter than the cylindrical portion 238 of the protector member 234. The drill guide 240 may also include a through hole or cannulated opening 246 extending along a longitudinal axis of the drill guide 240. The drill guide 240 may, for example, protect the surrounding soft tissue when a drill is inserted through the cannulated opening 246 to drill an opening for inserting the threaded member 250. The threaded member or implant 250 may include a head portion 252 at a first end of the threaded member 250 and cutting flutes 254 at a second end of the threaded member 250. The cutting flutes 254 may facilitate the insertion of the threaded member 250 into bones. In addition, the threaded member 250 may include a through hole or cannulated opening 256 extending through the threaded member 250 along a longitudinal axis. The through hole 256 may be configured or sized and shaped to receive the target pin 232. Alternatively, the threaded member 250 may be, for example, solid without a longitudinal opening. As shown, the threaded member 250 is threaded along the entire length, however, it is also contemplated that the threaded member 250 may be threaded along only a portion, for example, having partially or segmentally divided threads along the length.

The implant holder 260 may include a housing 262, a knob 274 and a locking member 280. The housing 262 may include an attachment arm 264 extending from and parallel to the housing 262 to form, for example, a U-shaped or hook like structure. The attachment arm 264 hooks under the bottom of the body 212 of the guide arm 210 to permit the sliding movement along the longitudinal axis of the body 212. A channel 266 is formed between the attachment arm 264 and the housing 262. The attachment arm 264 may also include at least one hole 268 extending through the attachment arm 264 from an exterior surface into the channel 266. The at least one hole 268 may be, for example, three holes. The implant holder 260 may also include an alignment post 270 extending away from a bottom surface of housing 262. The implant holder 260 may further include a through hole 272 extending through the housing 262 from a top surface to a bottom surface adjacent to the alignment post 270. The knob 274 may include an engagement protrusion 276 extending away from a back surface of the knob 274. The engagement protrusion 276 may be, for example, threaded to engage the at least one hole 268 to secure the implant holder 260 to the body 212 of the guide arm 210 at the desired position. The locking member 280 may include a shaft 282 with a knob 284 at a first end and a threaded portion 286 at a second end. The shaft 282 may be inserted through the through hole 272 of the housing 262 until the knob 284 contacts a top surface of the housing 262 and the threaded portion 286 extends past the bottom surface of the housing 262. The threaded portion 286 may engage a bone plate, such as bone plate 300, as described in greater detail below. The knob 274 may be rotated to insert the threaded portion 286 into the bone plate 300 and to remove the threaded portion 286 from the bone plate 300.

As shown in FIGS. 17-26, the guide pin 290 includes a shaft 292, a sphere 294, a tip 296, and a cylindrical protrusion 298. The sphere or spherical member 294 may be positioned between a first end and the tip 296. The tip 296 is threaded, however, it is also contemplated that the tip 296 may also have a smooth outer surface to facilitate insertion. The tip 296 is configured or sized and shaped to allow for the user to insert the guide pin 290 into a target bone either directly or through the skin. Once inserted into the target bone, the guide pin 290 may be secured to establish the target location for the threaded member 250. The sphere 294 is sized and shaped or configured to be inserted into the housing element 224 to allow for a full range of pivoting motions, as shown in FIGS. 17-22 and 27-29. The cylindrical protrusion 298 may be positioned adjacent to the sphere 294 between the sphere 294 and the tip 296.

The targeting guide assembly 200 may be assembled by inserting the guide pin 290 into the housing element 224 of the guide arm 210. The protector member 234 may be inserted into the through hole 222 of the guide arm 210 to receive the target pin 232. In addition, the implant holder 260 may be aligned with the body 212 of the guide arm 210 and secured in the desired position by engaging the engagement protrusion 276 with the body 212. The locking member 280 may be inserted into the opening 272 of the housing 262. Then, the alignment post 270 may be aligned with a corresponding alignment opening (not shown) in the bone plate 300 and the threaded portion 286 of the locking member 280 may engage a corresponding threaded opening (not shown) in the bone plate 300. In addition, the protector member 234 may be removed and the drill guide 240 may be inserted into the through hole 222 of the guide arm 210 over the target pin 232.

Figure 27:
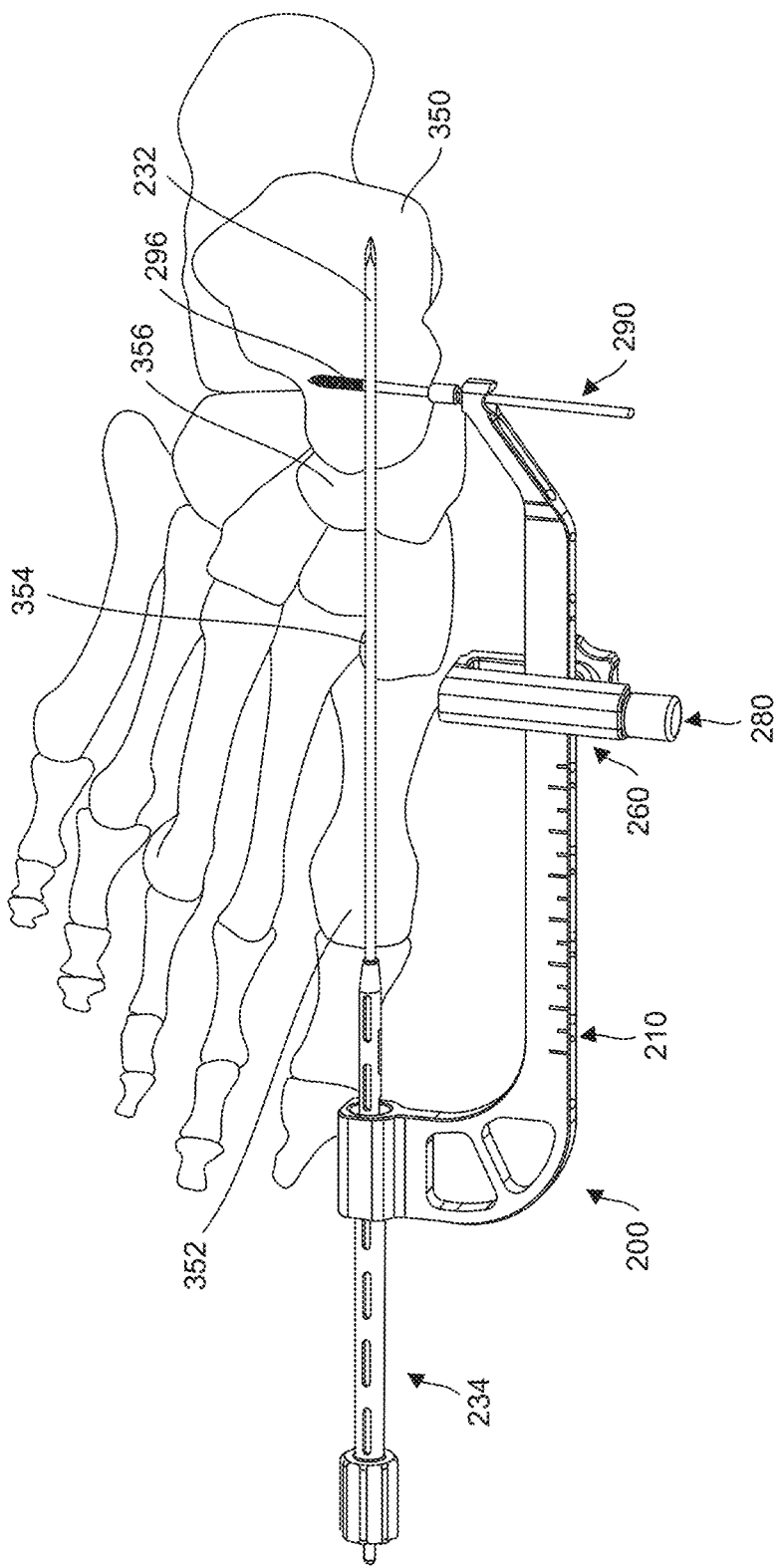
FIG. 27 is a dorsal view of the targeting guide system of FIG. 17 positioned on a foot, in accordance with an aspect of the present invention.
Figure 28:
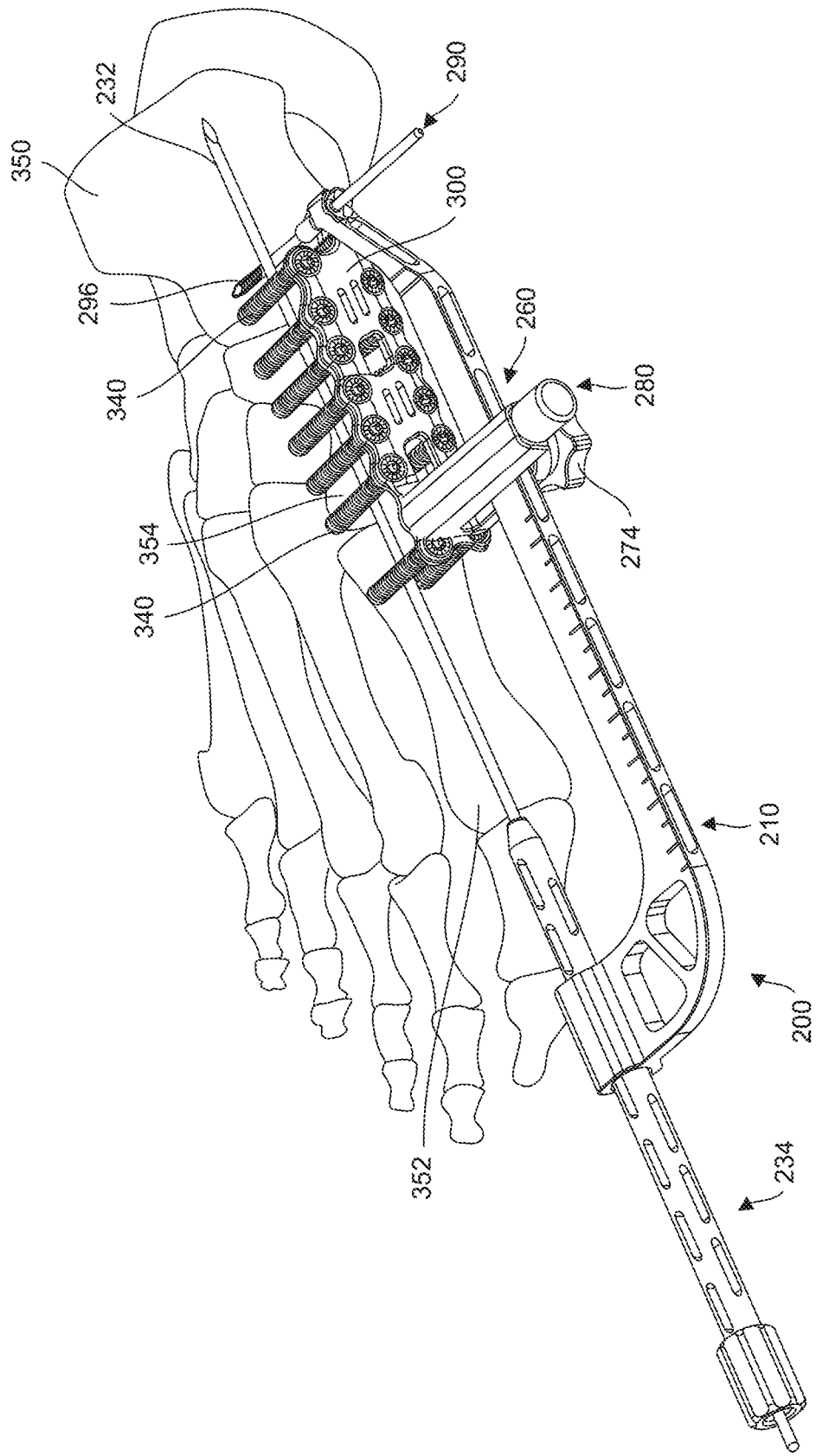
FIG. 28 is a perspective view of the foot and targeting guide system of FIG. 27 after a bone plate is secured to the foot with fasteners, in accordance with an aspect of the present invention.
Figure 29:
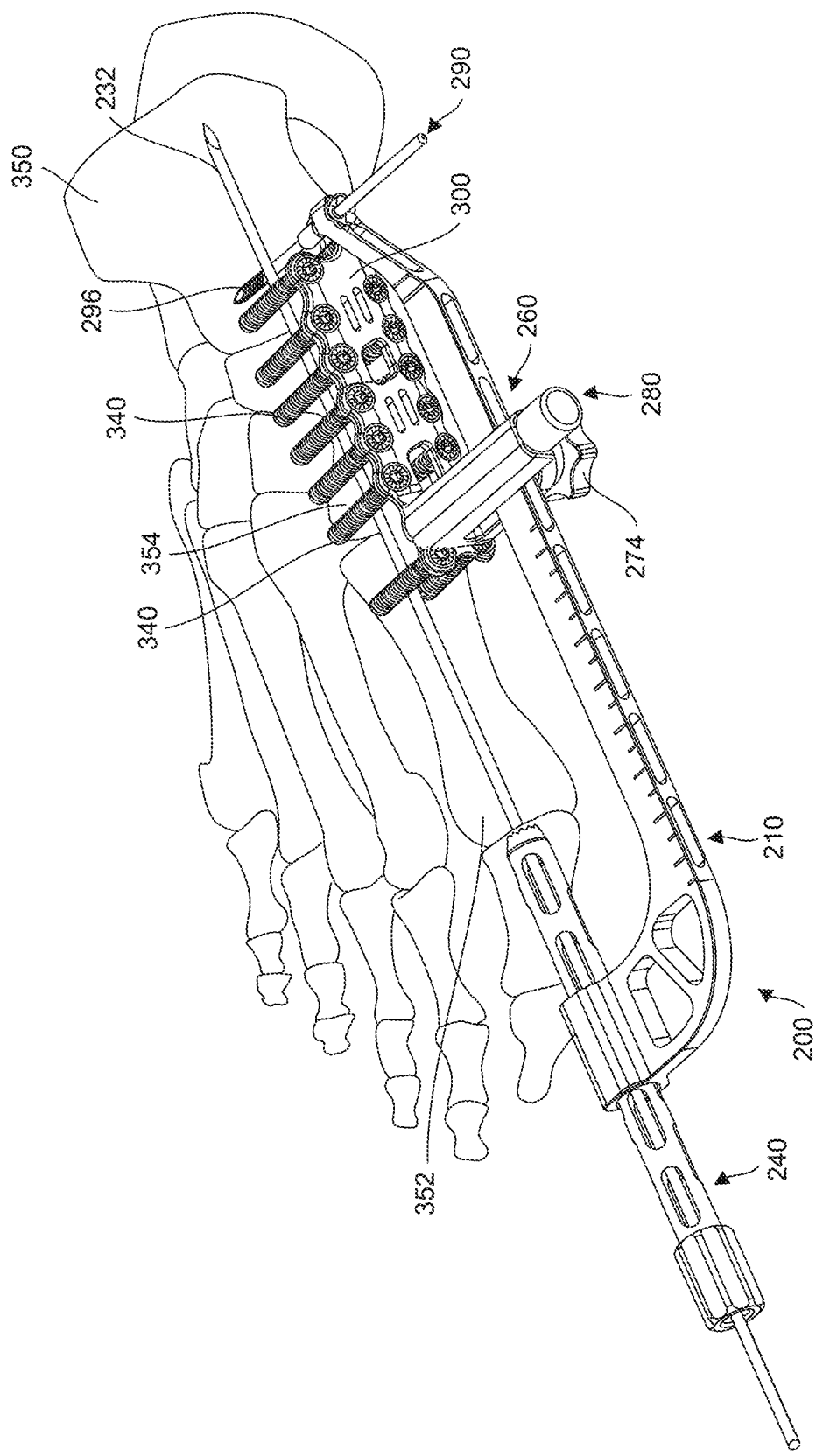
FIG. 29 is a perspective view of the foot and targeting guide system of FIG. 28 after removal of the protector member and insertion of the drill guide, in accordance with an aspect of the present invention.
Figure 30:
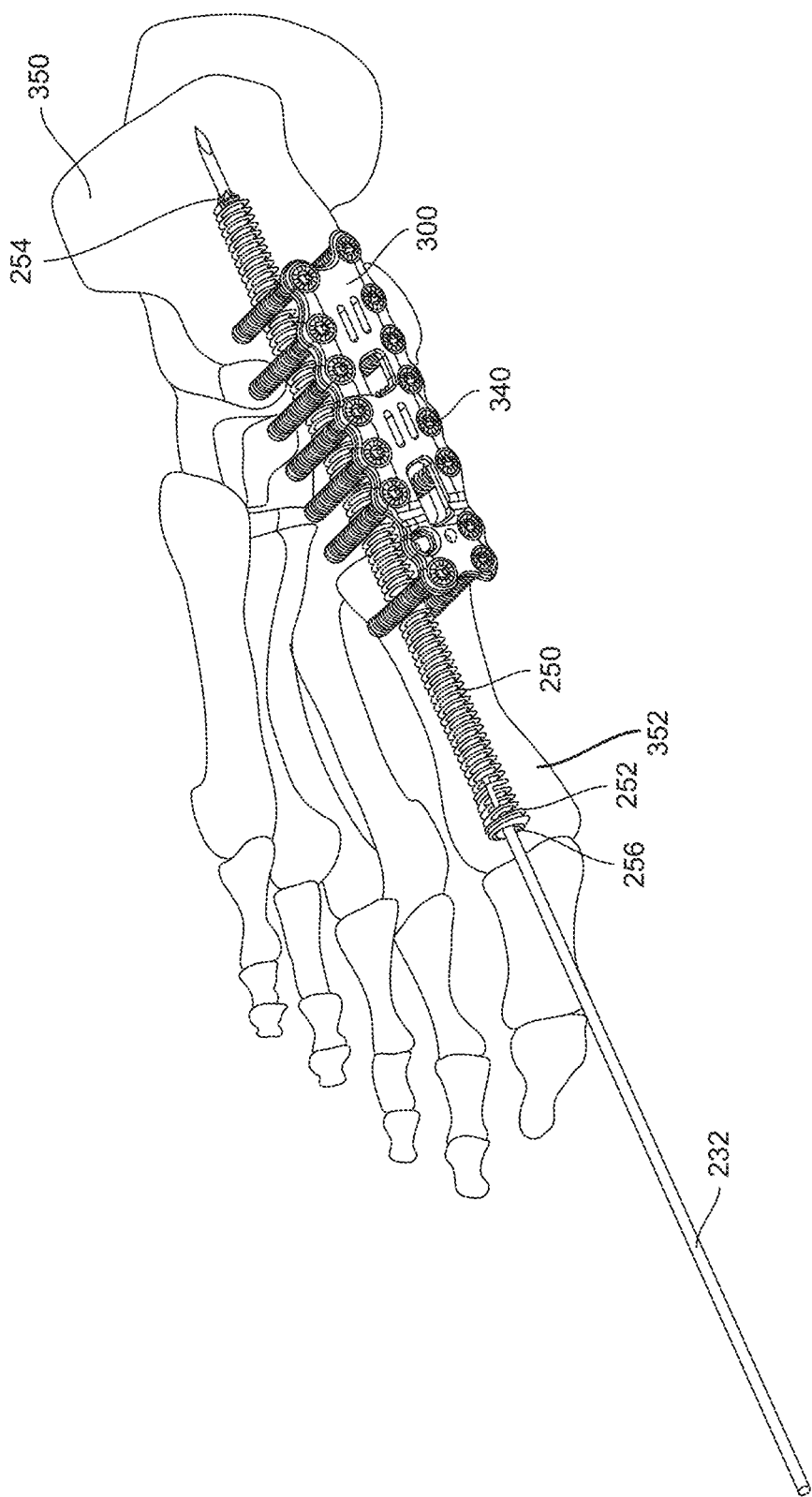
FIG. 30 is a perspective view of the foot of FIG. 29 after removal of the targeting guide system and insertion of a threaded member, in accordance with an aspect of the present invention.
Figure 31:
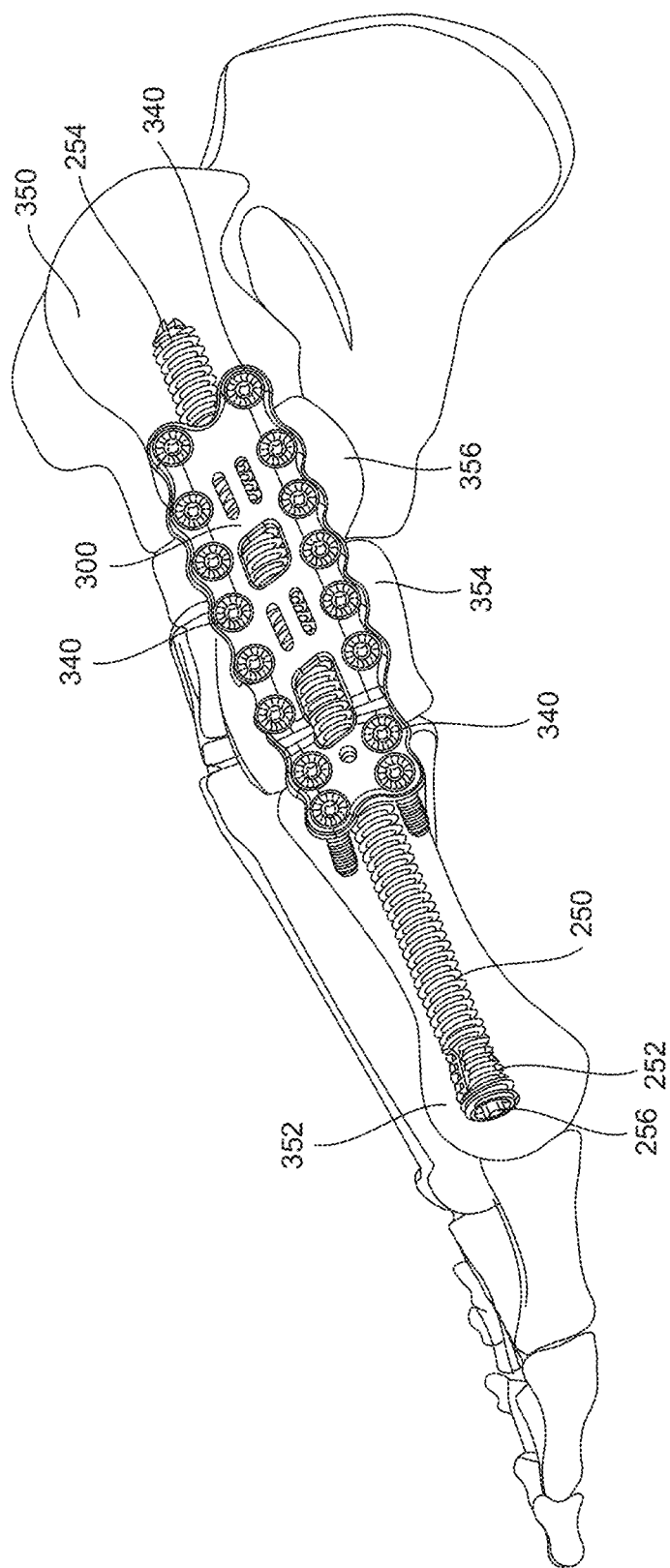
FIG. 31 is a side view of the foot of FIG. 30 after removal of the target pin, in accordance with an aspect of the present invention.

Referring now to FIGS. 27-31, a method for using the targeting guide assembly 200 to correct bone deformities is shown. The method may include, for example, performing an arthrodesis across at least one joint. The at least two bones of the at least one joint may be positioned in a desired final position and may be temporarily fixed. As shown in FIG. 27, the method may also include inserting a guide pin 290 into a first bone 350 to set the trajectory for the target pin 232 and the threaded member 250. Next, the housing element 224 of the guide arm 210 may be coupled to the sphere 294 of the guide pin 290. The guide arm 210 may be rotated about the sphere 294 to position the first end 214 of the guide arm 210 with respect to a second bone 352. Next, the protector member 234 may be inserted into the through hole 222 and a target pin 232 may be inserted through the protector member 234 and into at least one bone 352, 354, 356, 350. The trajectory of the target pin 232 will overlap or engage the guide pin 290. In one embodiment, the implant holder 260 may be coupled to the guide arm 210 before the guide arm 210 is coupled to the guide pin 290. Alternatively, the implant holder 260 may be coupled to the guide arm 210 after the target pin 232 is inserted into the bones 352, 354, 356, 350. The bone plate 300 may then be coupled to the implant holder 260 and aligned on the bones 352, 354, 356, 350, as shown in FIG. 28. It is also contemplated that the bone plate 300 may be coupled to the implant holder 260 prior to the guide arm 210 being coupled to the guide pin 290. Once the bone plate 300 is coupled to the implant holder 260, the position of the implant 300 may be adjusted along the length of the guide arm 210 to allow for implant positioning in a first plane, for example, the sagittal plane. The guide arm 210 may alternatively or in addition to adjustment along the length be rotated around the guide pin 290 to rotate the bone plate 300 in a second plane, for example, the frontal plane. Movement of the bone plate 300 in the two planes allows for fixation devices or bone screws 340 to be inserted with a trajectory to avoid contacting the target pin 232 and/or threaded member 250. The bone plate 300 may be secured to the bones 352, 354, 356, 350 with bone fasteners 340 inserted to avoid contacting the target pin 232 and the threaded member 250 when inserted. The bone fasteners or fixation devices 340 may be, for example, locking or non-locking fasteners. The method may then include removing the protector member 234 by sliding the protector member 234 out of the through hole 222 of the guide arm 210 over the target pin 232. As shown in FIG. 29, the drill guide 240 may then be inserted through the through hole 222 over the target pin 232 and positioned onto a bone 352. A cannulated drill may be used to drill over the target pin 232. The cannulated drill and drill guide 240 may then be removed from the guide arm 210 and the threaded member 250 may be inserted over the target pin 232 and into the bones 352, 354, 356, 350, as shown in FIG. 30. Although not shown, it is also contemplated that the bone plate 300 may be coupled to the bones 352, 354, 356, 350 after the threaded member 250 is inserted into the bones 352, 354, 356, 350. As also shown in FIG. 30, the guide arm 210 and guide pin 290 may be removed from the bones 352, 354, 356, 350. Finally, as shown in FIG. 31, the target pin 232 may be removed from the bones 352, 354, 356, 350 and the threaded member 250.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of FIGS. 1-16 and FIGS. 17-31 may be used interchangeably and in alternative combinations as would be modified or altered by one of skill in the art. Further, the steps of the surgical methods associated with FIGS. 1-16 and FIGS. 17-31 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiment, the invention is now claimed to be:

1. A surgical method, comprising:
    inserting a guide pin into a bone;
    securing a guide arm to the guide pin at a second end of the guide arm;
    inserting a protector member into a first end of the guide arm;
    inserting a target pin through at least two bone segments;
    rotating the guide arm about a spherical component such that the first end of the guide arm is in a first position relative to a first bone segment of the at least two bone segments;
    removing the protector member from the guide arm;
    drilling a hole over the target pin; and
    threading a target member into a drill hole to secure the at least two bone segment.

2. The method of claim 1, wherein the at least two bone segments comprise at least one of a talus and a first metatarsal of a patient.

3. The method of claim 1, wherein the guide pin comprises the spherical component disposed at a position along a length of the guide pin.

4. The method of claim 3, wherein the guide arm comprises a housing element;
    wherein securing the guide arm to the guide pin comprises coupling the housing element with the spherical component of a guide wire.

5. The method of claim 1, further comprising inserting the protector member into a through hole of the first end of the guide arm.

6. The method of claim 1, further comprising inserting the target pin through the protector member and into at least one of the first bone segment and the second bone segment of the at least two bone segments.

7. The method of claim 6, wherein the guide pin is inserted at a first trajectory and the target pin is inserted at a second trajectory;
    wherein the first and second trajectories overlap.

8. The method of claim 7, wherein the guide pin and the second trajectory engage one another.

9. The method of claim 1, further comprising coupling an implant holder to the guide arm.

10. The method of claim 9, further comprising coupling a bone plate with the implant holder and aligning the implant holder adjacent at least one of the first bone segment and the second bone segment of the at least two bone segments.

11. The method of claim 10, further comprising adjusting a position of the bone plate to a desired position in a first plane along relative to the guide arm.

12. The method of claim 11, further comprising rotating the guide arm about the guide pin to adjust the position of the bone plate to a desired position in a second plane relative to the guide arm.

13. The method of claim 12, wherein the desired position of the bone plate in the first and second planes relative to the guide arm is configured to position one or more through holes of the bone plate to accommodate one or more fixation components therethrough at a trajectory to avoid contacting the target pin.

14. The method of claim 13, further comprising securing the bone plate to at least one of the first and second bone segment such that the one or more fixation components avoid contacting the targeting pin or a path of a threaded member.

15. A surgical method, comprising:
    inserting a guide pin into a bone;
    securing a guide arm to the guide pin at a second end of the guide arm;
    inserting a protector member into a first end of the guide arm;
    inserting a target pin through at least two bone segment;
    removing the protector member from the guide arm;
    coupling a bone plate with an implant holder coupled to the guide arm;
    adjusting the bone plate along a length of the guide arm in a first plane;
    drilling a hole over the target pin; and
    threading a target member into a drill hole to secure the at least two bone segments.

16. The surgical method of claim 15, further comprising:
    rotating the guide arm around the guide pin to rotate the bone plate in a second plane.

* * * * *